United States Patent
Pasricha et al.

(10) Patent No.: US 11,136,322 B2
(45) Date of Patent: *Oct. 5, 2021

(54) PERIPHERALLY RESTRICTED GABA POSITIVE ALLOSTERIC MODULATORS FOR THE TREATMENT OF IRRITABLE BOWEL SYNDROME AND OTHER AILMENTS OF THE PERIPHERAL NERVOUS SYSTEM

(71) Applicants: THE JOHNS HOPKINS UNIVERSITY, Baltimore, MD (US); LIEBER INSTITUTE, INC., Baltimore, MD (US)

(72) Inventors: Pankaj Pasricha, Ellicott City, MD (US); Yifang Huang, Lansdale, PA (US); James Barrow, Arnold, MD (US)

(73) Assignees: The Johns Hopkins University, Baltimore, MD (US); Lieber Institute, Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/291,403

(22) Filed: Mar. 4, 2019

(65) Prior Publication Data

US 2020/0062759 A1 Feb. 27, 2020

Related U.S. Application Data

(63) Continuation of application No. 15/320,866, filed as application No. PCT/US2015/037913 on Jun. 26, 2015, now Pat. No. 10,266,534.

(60) Provisional application No. 62/017,418, filed on Jun. 26, 2014.

(51) Int. Cl.
| | | |
|---|---|---|
| *A61K 31/5517* | (2006.01) | |
| *A61P 25/00* | (2006.01) | |
| *C07D 487/04* | (2006.01) | |
| *C07D 243/12* | (2006.01) | |
| *A61K 45/06* | (2006.01) | |
| *A61K 31/5513* | (2006.01) | |
| *C07D 243/24* | (2006.01) | |

(52) U.S. Cl.
CPC ........ *C07D 487/04* (2013.01); *A61K 31/5513* (2013.01); *A61K 31/5517* (2013.01); *A61K 45/06* (2013.01); *C07D 243/12* (2013.01); *C07D 243/24* (2013.01)

(58) Field of Classification Search
CPC .... A61K 31/5517; A61P 25/00; C07D 487/04
See application file for complete search history.

(56) References Cited

U.S. PATENT DOCUMENTS

| | | | |
|---|---|---|---|
| 3,703,510 A | 11/1972 | Earley et al. | |
| 3,763,179 A | 10/1973 | Gall et al. | |
| 3,784,556 A | 1/1974 | Gagneux et al. | |
| 3,852,300 A | 12/1974 | Gagneux et al. | |
| 3,852,461 A | 12/1974 | Hester, Jr. et al. | |
| 3,927,016 A | 12/1975 | Hester, Jr. et al. | |
| 4,027,029 A | 5/1977 | Gagneux et al. | |
| 4,046,772 A | 9/1977 | Kuwada et al. | |
| 6,174,881 B1 | 1/2001 | Borer et al. | |
| 8,835,424 B2 | 9/2014 | Cook et al. | |
| 10,266,534 B2 | 4/2019 | Pankaj et al. | |
| 2009/0163451 A1 | 6/2009 | Porreca et al. | |
| 2010/0317619 A1 | 12/2010 | Cook et al. | |
| 2017/0197967 A1 | 7/2017 | Pankaj et al. | |

FOREIGN PATENT DOCUMENTS

| | | |
|---|---|---|
| GB | 1389434 | 4/1975 |
| GB | 1497827 A | 1/1978 |
| JP | 49101396 | 9/1974 |
| JP | S50140492 | 11/1975 |
| JP | 2009/525392 | 7/2009 |
| WO | 1996/23790 | 8/1996 |
| WO | 2008073130 A1 | 6/2008 |
| WO | 2013-009625 A1 | 1/2013 |

OTHER PUBLICATIONS

Castedal, M. et al. "Effects of midazolam on small bowel motility in humans" Alimentary Pharmacology and Therapeutics, 2000, vol. 14, No. 5, pp. 571-578.

Tehrani, M. H. J. et al., "Agonist-Dependent Internalization of γ-Aminobutyric AcidA/Benzodiazepine Receptors in Chick Cortical Neurons", Journal of neurochemistry, 1991, vol. 57, No. 4, pp. 1307-1312.

Burenkova, N. A., et al. "Synthesis and selectivity of 1-methoxycarbonylmethyl-3-arylamino-7-bromo-5-phenyl-1, 2-dihydro-3H-1, 4-benzodiazepin-2-ones binding for CNS benzodiazepine receptors", Ukrainica Bioorganica Acta, 2009, vol. 7, No. 1, pp. 8-15.

Mazurov, A. A., et al. "Basic hydrolysis of 3-acetoxy-7-bromo-5-(ochlorophenyl)-1-ethoxycarbonylmethyl-1, 2-dihydro-3H-1, 4-benzadiazepin-2-one", Chemistry of Heterocyclic Compounds, 1990, vol. 26, No. 5, pp. 582-587.

(Continued)

*Primary Examiner* — Brenda L Coleman

(74) *Attorney, Agent, or Firm* — Fish & Richardson P.C.

(57) ABSTRACT

The present invention provides compounds and compositions which are positive allosteric modulators of GABA-A receptors that selectively target the peripheral nervous system and organs of the body, and which do not pass through the blood-brain barrier. The compounds and compositions of the present invention are useful for treatment of diseases or disorders which are mediated by GABA-A neuronal activity, such as, for example, visceral pain, gut motility, irritable bowel syndrome, functional abdominal pain, functional idiopathic diarrhea, inflammatory bowel diseases, drug induced pain, bile salt malabsorption, lactase or other carbohydrate intolerance.

22 Claims, 3 Drawing Sheets

(56) References Cited

OTHER PUBLICATIONS

Koike, M. et al., "Structure determination of metabolites of rilmazafone, a 1H-1,2,4-triazolylbenzophenone derivative in monkey urine", Xenobiotica, 1988, vol. 18, No. 3, pp. 257-268.
CAS printout of JP 49101396, 2018.
Makaron, L., et al., "Cognition-impairing effects of benzodiazepine-type drugs: role of GABAA receptor subtypes in an executive function task in rhesus monkeys".
Extended European search report dated Nov. 29, 2017 for EP application 15811321.7.
PCT International Search Report and Written Opinion in International Appln. No. PCT/US2015/037913, dated Mar. 31, 2016, 18 pages.
PCT International Preliminary Report on Patentability in International Appln. No. PCT/US2015/037913, dated Jan. 5, 2017, 13 pages.

PERIPHERALLY RESTRICTED GABA POSITIVE ALLOSTERIC MODULATORS FOR THE TREATMENT OF IRRITABLE BOWEL SYNDROME AND OTHER AILMENTS OF THE PERIPHERAL NERVOUS SYSTEM

REFERENCE TO RELATED APPLICATIONS

This application is a Continuation of U.S. patent application Ser. No. 15/320,866, filed Dec. 21, 2016, which is a 35 U.S.C. § 371 U.S. national entry of International Application PCT/US2015/037913, having an international filing date of Jun. 26, 2015, which claims the benefit of U.S. Provisional Patent Application No. 62/017,418, filed on Jun. 26, 2014, the content of each of the aforementioned applications is herein incorporated by reference in their entirety.

FIELD OF THE INVENTION

This invention relates to compounds which are positive allosteric modulators of GABA-A receptors that are peripherally restricted. The compounds of the present invention can be useful in the treatment of systemic diseases of the body which can be modulated by the use of compounds which are positive allosteric modulators of GABA-A receptors that are peripherally restricted. In some embodiments, the compounds of the present invention can be useful in the treatment of diseases such as irritable bowel syndrome. More specifically, the invention relates to compounds and methods for the treatment of irritable bowel syndrome, where such compounds comprise pharmaceutically acceptable amounts of a peripherally-restricted GABA-A receptor positive allosteric modulator.

BACKGROUND OF THE INVENTION

This invention focuses on the development of compounds which are positive allosteric modulators of GABA-A receptors that are peripherally restricted, and their use in the treatment of disease. In some embodiments, the compounds of the present invention are useful in the treatment of irritable bowel syndrome (IBS), a disorder that is defined clinically by intermittent abdominal pain in association with altered bowel movements in the absence of any other structural or inflammatory cause. Based on the dominant bowel pattern, IBS patients are clinically phenotyped into three categories: IBS-D (diarrhea predominant), IBS-C (constipation predominant), and IBS-M (mixed or alternating between diarrhea and constipation). IBS is a very common medical disorder with a prevalence estimated between 6-20% in most developed countries and associated with significant impairment of quality of life and socioeconomic costs estimated in the billions of dollars every year.[1] Unfortunately, there are few therapeutic options available for patients, with only two approved drugs (lubiprostone and linaclotide) that are both secretagogues and indicated only for symptomatic relief of IBS-C. There are currently no approved prescription drugs for treatment of IBS-D.

The pathogenesis of IBS-D (as with other forms of IBS) remains poorly understood but is thought to be associated with hyperexcitability of neurons, affecting both extrinsic (spinal) and intrinsic (enteric) nerves leading to chronic visceral hypersensitivity and altered motility, respectively. As compared with controls, patients with IBS show increased colonic myoelectrical activity both at baseline and after a meal.[2] Suppression of such excitability is therefore a logical therapeutic target. Most pharmacological approaches to the treatment of IBS focus on the role of serotonin (5-HT), released from chemo- and mechanosensitive enterochromaffin cells residing in the mucosa, leading to activation of nociceptive nerves as well as intrinsic primary afferent neurons (IPANs) in the enteric nervous system (ENS) to initiate reflexes for motility and secretion.[3] Unfortunately, 5-HT receptor modulators (e.g. tegaserod or alosetron) have only been modestly effective and associated with significant adverse effects leading to their withdrawal from the general market. There is therefore a great need for alternative approaches.[4]

Gamma Aminobutyric Acid (GABA) is the most important inhibitory neurotransmitter in the central nervous system (CNS). Activation of neuronal GABA receptors results in hyperpolarization and stabilization of neuronal excitability. GABA-ergic neurons are also abundant in the enteric nervous system and both GABA-A (inotropic) and GABA-B (metabotropic) receptors are present in the gut, mediating distinct functional effects.[5-13] GABA-B receptor agonists have been investigated for treatment of IBS.[14]

It is thought that the therapeutic benefit of brain penetrating GABA-A modulating benzodiazepines, such as diazepam, in IBS results predominantly from the relief of anxiety that often accompanies IBS.[17] The use of brain penetrating benzodiazepines (or other brain penetrating compounds), however, is clinically problematic both because of sedation, and the potential for addiction and physical dependence on chronic use. An alternate approach has been described for tofisopam and its isomer, dextofisopam which is currently under study for IBS. These molecules have been classified as atypical benzodiazepines which enter the CNS and bind to a novel binding site within the central nervous system that may be responsible for mediating its actions.[18][19]

GABA-A receptor positive allosteric modulators have heretofore been concerned with CNS conditions like anxiety, insomnia, and epilepsy not IBS.

SUMMARY OF THE INVENTION

The present invention provides compounds and compositions which are positive allosteric modulators of GABA-A receptors that selectively target the peripheral nervous system and organs of the body, and which do not pass through the blood-brain barrier. The compounds and compositions of the present invention are useful for treatment of diseases or disorders which are mediated by GABA-A neuronal activity, such as, for example, visceral pain, gut motility, irritable bowel syndrome, functional abdominal pain, functional idiopathic diarrhea, inflammatory bowel diseases, drug induced pain, bile salt malabsorption, lactase or other carbohydrate intolerance.

In an embodiment, the present invention provides compounds which are GABA-A receptor positive allosteric modulators that are peripherally-restricted to the GABAergic neurons of the body outside of the brain and central nervous system.

In accordance with an embodiment, the present invention provides a compound of formulas 1 and 2:

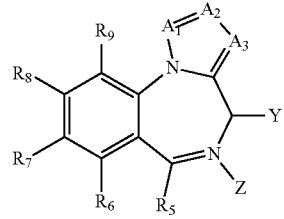

(1)

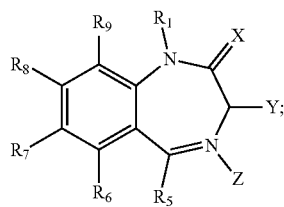

(2)

wherein, $A_1$, $A_2$, and $A_3$ are independently selected from C or N, where at least one of $A_1$, $A_2$, or $A_3$ is a C unsubstituted or substituted with a group consisting of alkyl, alkenyl, alkynyl, cycloalkyl, heterocycloalkyl, aryl, heteroaryl, —$COOR_{10}$, —$COR_{10}$, —$OR_{10}$, —$SR_{10}$, —$NR_{10}R_{11}$, and —$CONR_{10}R_{11}$;

each of $R_{10}$ and $R_{11}$ is independently H, alkyl, alkenyl, alkynyl, cycloalkyl, heterocycloalkyl, aryl, or heteroaryl optionally substituted with one or more amidinyl, guanidinyl, phosphate, sulfate, tetrazole, 3-hydroxyisoxazole, quaternary ammonium salts including urea, primary amides, sulfonamides, sulfonyl ureas, acylamidines, acylguanidines, or —$NR_{12}R_{13}$ groups; each of $R_{12}$ and $R_{13}$ is independently H, —$CONH_2$, —$SOONH_2$, alkyl, alkenyl, alkynyl, cycloalkyl, heterocycloalkyl, aryl, or heteroaryl;

X is O;

Y is selected from H, OH, OQ, and $CO_2Q$ where Q is a prodrug that liberates Y=H or Y=OH;

Z is selected from oxygen and an electron lone pair;

$R_1$ is alkyl, alkenyl, alkynyl, cycloalkyl, heterocycloalkyl, aryl, heteroaryl optionally substituted with one or more halo, $CF_3$, CN, $NO_2$, COOH, $C_{1-4}$ alkyl, $C_{2-4}$ alkenyl, $C_{1-4}$ alkynyl, OH, OR (where OR is $C_{1-4}$ alkyl or $C_{1-4}$ fluoroalkyl), $SO_2R$ (where R is $C_{1-4}$ alkyl or $C_{1-4}$ fluoroalkyl);

$R_5$ is selected from the group consisting of aryl, heteroaryl, or cycloalkenyl groups optionally substituted with one or more halo, $CF_3$, CN, $NO_2$, $C_{1-4}$ alkyl, $C_{2-4}$ alkenyl, $C_{1-4}$ alkynyl, OH, OR (where OR is $C_{1-4}$ alkyl or $C_{1-4}$ fluoroalkyl), and $SO_2R$ (where R is $C_{1-4}$ alkyl or $C_{1-4}$ fluoroalkyl); and $R_6$, $R_7$, $R_8$, $R_9$ are each independently selected from the group consisting of H, halo, $CF_3$, CN, $NO_2$, $C_{1-4}$ alkyl, $C_{2-4}$ alkenyl, $C_{1-4}$ alkynyl, OH, OR (where OR is $C_{1-4}$ alkyl or $C_{1-4}$ fluoroalkyl), and $SO_2R$ (where R is $C_{1-4}$ alkyl or $C_{1-4}$ fluoroalkyl) compounds.

In accordance with another embodiment, the present invention provides methods and uses of the inventive compounds for positive modulation of GABA-A receptors in tissues and organs outside the brain.

In accordance with a further embodiment, the present invention provides compounds and methods for treating or preventing visceral pain and modulating gut motility, such as in irritable bowel syndrome, in a subject comprising the administration of a therapeutically effective amount of a peripherally-restricted GABA-A receptor positive allosteric modulator.

In accordance with an embodiment, the present invention compounds for positive modulation of GABA-A receptors in tissues and organs outside the brain selected from the group consisting of:

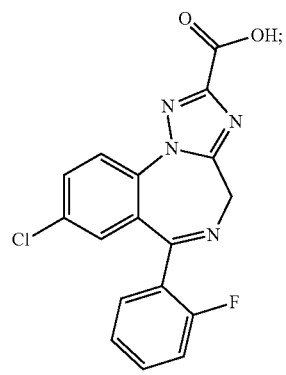

(Compound 1)

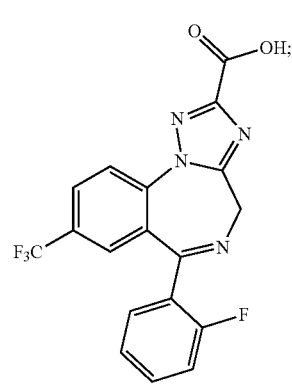

(Compound 2)

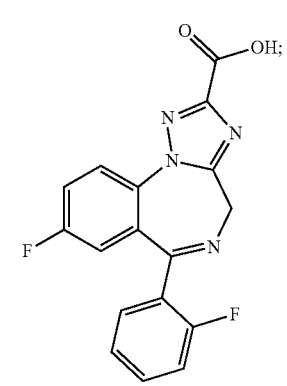

(Compound 3)

-continued
(Compound 4)
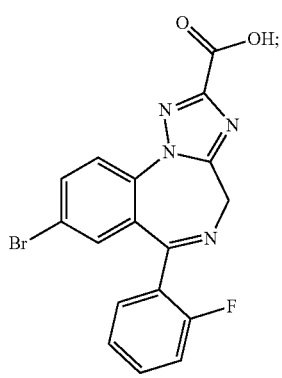
(Compound 8)
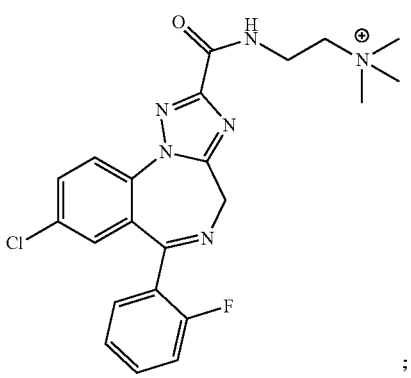
(Compound 5)
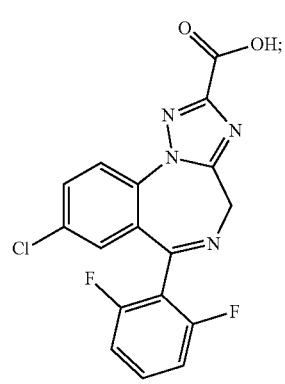
(Compound 9)
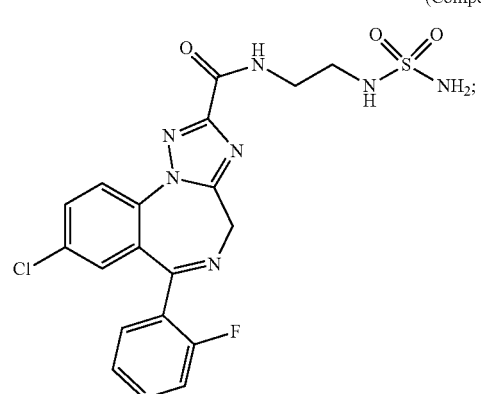
(Compound 6)
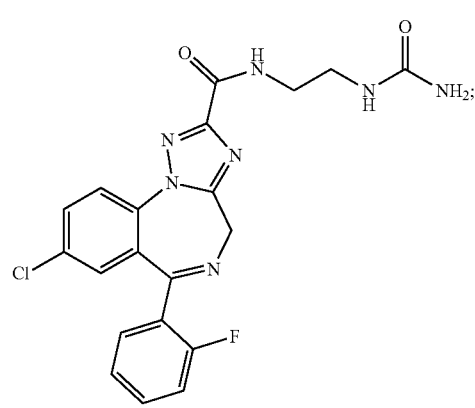
(Compound 10)
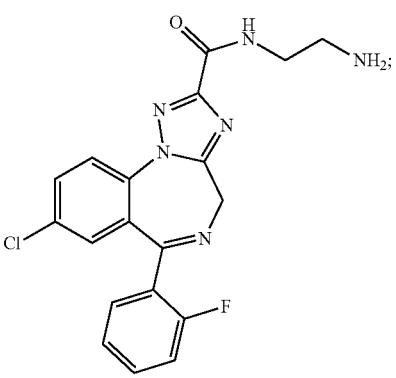
(Compound 7)
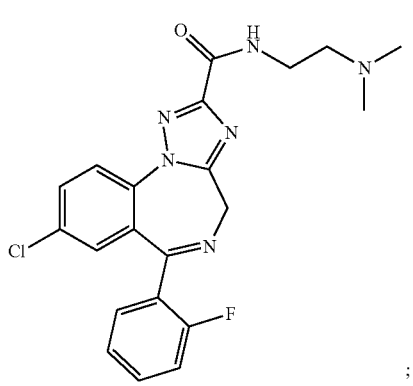
(Compound 11)
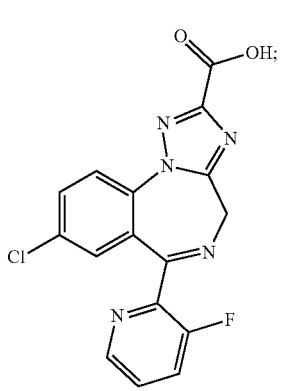

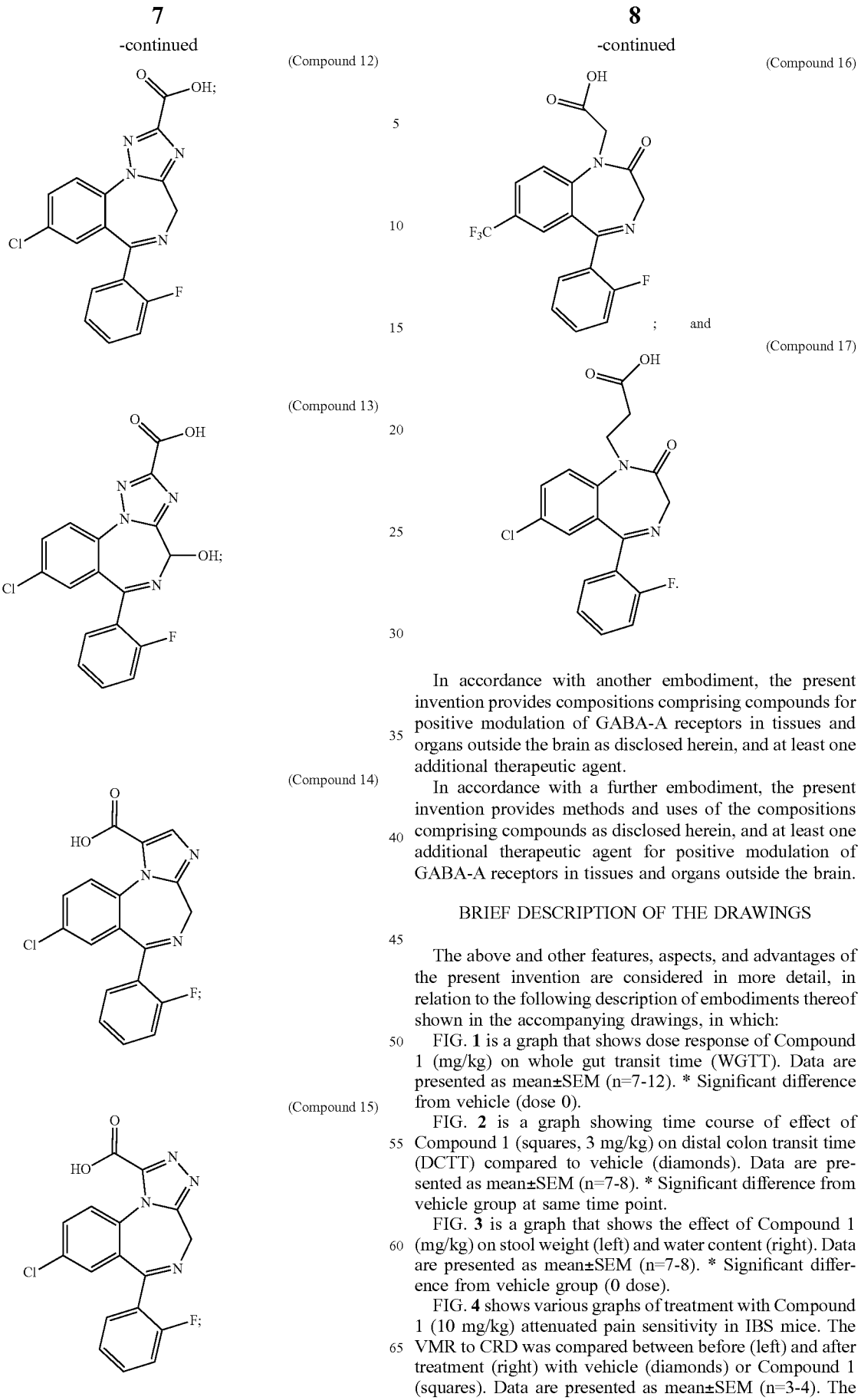

In accordance with another embodiment, the present invention provides compositions comprising compounds for positive modulation of GABA-A receptors in tissues and organs outside the brain as disclosed herein, and at least one additional therapeutic agent.

In accordance with a further embodiment, the present invention provides methods and uses of the compositions comprising compounds as disclosed herein, and at least one additional therapeutic agent for positive modulation of GABA-A receptors in tissues and organs outside the brain.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION OF THE INVENTION

Figure 1:
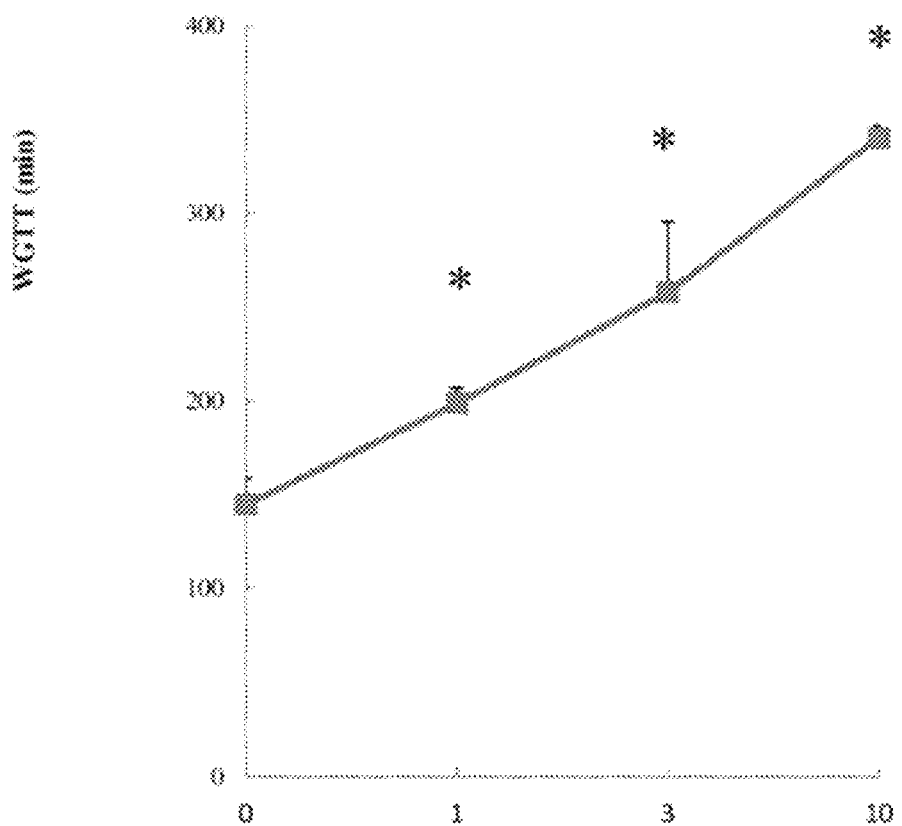
FIG. 1 is a graph that shows dose response of Compound 1 (mg/kg) on whole gut transit time (WGTT). Data are presented as mean±SEM (n=7-12). * Significant difference from vehicle (dose 0).

The invention summarized above may be better understood by referring to the following description. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Overview

In accordance with an embodiment, the present invention provides methods for treatment of visceral pain and modulating gut motility in a subject, such as that caused by IBS, by positively modulating the GABA-A receptor in the enteric nervous system without the usual CNS side effects of GABA modulation is provided. It is contemplated that the methods described herein are effective in treating visceral pain caused by other ailments, not only IBS. Examples of non-IBS related ailments which can be treated by the inventive methods, include functional abdominal pain, functional idiopathic diarrhea, inflammatory bowel diseases, drug induced pain, bile salt malabsorption, lactase or other carbohydrate intolerance. Through modulation of physical properties such as membrane permeability and incorporation of functional groups known to enhance recognition by blood-brain barrier transporters, GABA-A receptor positive allosteric modulators used in the present invention, are restricted from the CNS so they do not produce unwanted side effects such as sedation yet still exert beneficial pharmacological effects on the enteric nervous system.

Pharmacological access to the CNS is restricted by the blood brain barrier (BBB), a system that includes tight junctions between vascular endothelial cells and membrane transporters which work to minimize brain exposure of many circulating biomolecules, peptides, and drugs. Several therapeutically useful drugs take advantage of this restriction to provide a peripheral benefit without CNS complications, such as the well-known non-sedating antihistamines loratadine and cetirizine.[20] Since all of the known GABA-A positive allosteric modulators, such as diazepam and midazolam, were designed to treat CNS disorders; non-brain-penetrating analogs have not been previously described, or only described as intermediates toward more useful compounds.

In accordance with some embodiments, the present invention provides chemical compounds according to formulas 1 and 2, and pharmaceutically acceptable salts, solvates, and stereoisomers thereof, or any prodrug equivalents (such as esters) thereof, where at least one of the R or A substituents contain a functional group that reduces blood-brain barrier permeability, as shown below.

In accordance with an embodiment, the present invention provides a compound of formulas 1 and 2:

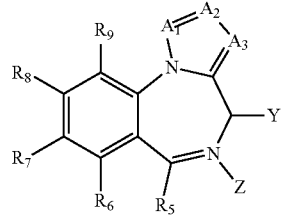

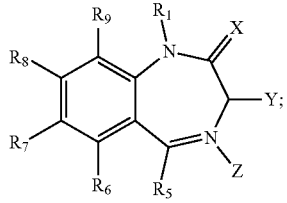

wherein, $A_1$, $A_2$, and $A_3$ are independently selected from C or N, where at least one of $A_1$, $A_2$, or $A_3$ is a C unsubstituted or substituted with a group consisting of alkyl, alkenyl, alkynyl, cycloalkyl, heterocycloalkyl, aryl, heteroaryl, $-COOR_{10}$, $-COR_{10}$, $-OR_{10}$, $-SR_{10}$, $-NR_{10}R_{11}$, and $-CONR_{10}R_{11}$;

each of $R_{10}$ and $R_{11}$ is independently H, alkyl, alkenyl, alkynyl, cycloalkyl, heterocycloalkyl, aryl, or heteroaryl optionally substituted with one or more amidinyl, guanidinyl, phosphate, sulfate, tetrazole, 3-hydroxyisoxazole, quaternary ammonium salts including urea, primary amides, sulfonamides, sulfonyl ureas, acylamidines, acylguanidines, or $-NR_{12}R_{13}$ groups;

each of $R_{12}$ and $R_{13}$ is independently H, $-CONH_2$, $-SOONH_2$, alkyl, alkenyl, alkynyl, cycloalkyl, heterocycloalkyl, aryl, or heteroaryl;

X is O;

Y is selected from H, OH, OQ, and $CO_2Q$ where Q is a prodrug that liberates Y=H or Y=OH;

Z is selected from oxygen and an electron lone pair;

$R_1$ is alkyl, alkenyl, alkynyl, cycloalkyl, heterocycloalkyl, aryl, heteroaryl optionally substituted with one or more halo, $CF_3$, CN, $NO_2$, COOH, $C_{1-4}$ alkyl, $C_{2-4}$ alkenyl, $C_{1-4}$ alkynyl, OH, OR (where OR is $C_{1-4}$ alkyl or $C_{1-4}$ fluoroalkyl), $SO_2R$ (where R is $C_{1-4}$ alkyl or $C_{1-4}$ fluoroalkyl);

$R_5$ is selected from the group consisting of aryl, heteroaryl, or cycloalkenyl groups optionally substituted with one or more halo, $CF_3$, CN, $NO_2$, $C_{1-4}$ alkyl, $C_{2-4}$ alkenyl, $C_{1-4}$ alkynyl, OH, OR (where OR is $C_{1-4}$ alkyl or $C_{1-4}$ fluoroalkyl), and $SO_2R$ (where R is $C_{1-4}$ alkyl or $C_{1-4}$ fluoroalkyl); and $R_6$, $R_7$, $R_8$, $R_9$ are each independently selected from the group consisting of H, halo, $CF_3$, CN, $NO_2$, $C_{1-4}$ alkyl, $C_{2-4}$ alkenyl, $C_{1-4}$ alkynyl, OH, OR (where OR is $C_{1-4}$ alkyl or $C_{1-4}$ fluoroalkyl), and $SO_2R$ (where R is $C_{1-4}$ alkyl or $C_{1-4}$ fluoroalkyl) compounds.

In accordance with an embodiment, the present invention provides compounds of formula 1 for positive modulation of GABA-A receptors in tissues and organs outside the brain selected from the group consisting of:

(Compound 1)
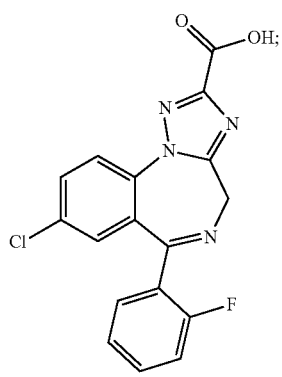
(Compound 5)
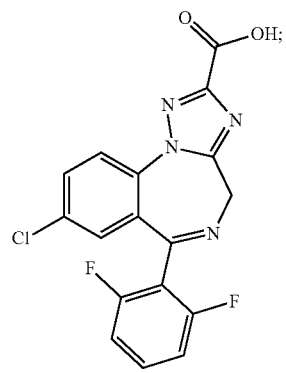
(Compound 2)
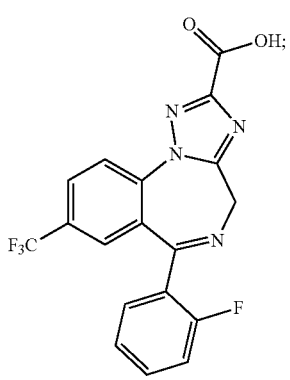
(Compound 6)
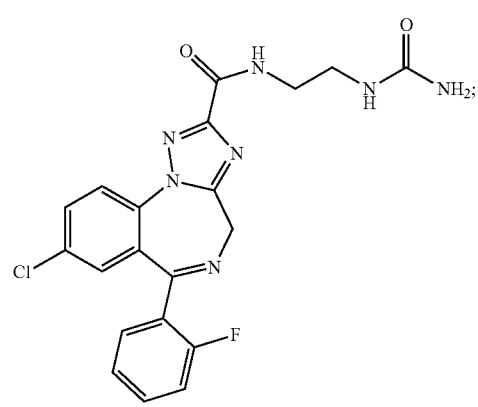
(Compound 3)
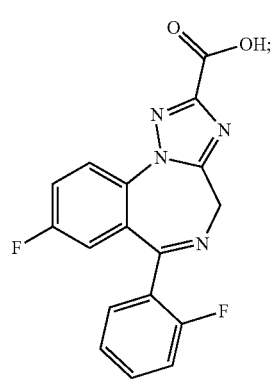
(Compound 7)
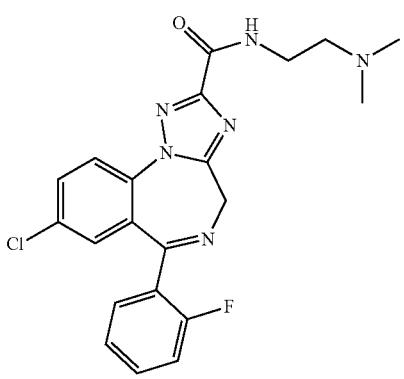
(Compound 4)
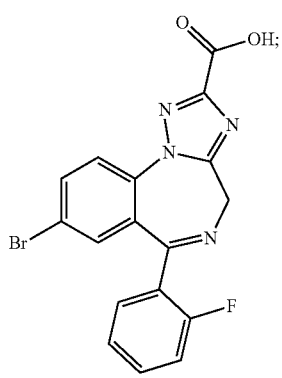
(Compound 8)
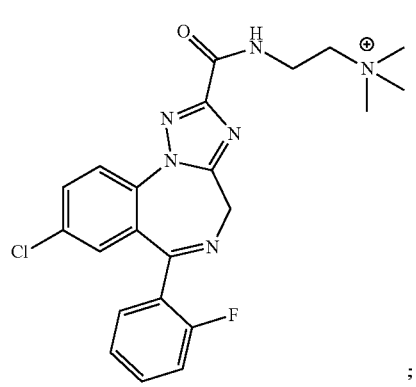

-continued
(Compound 9)
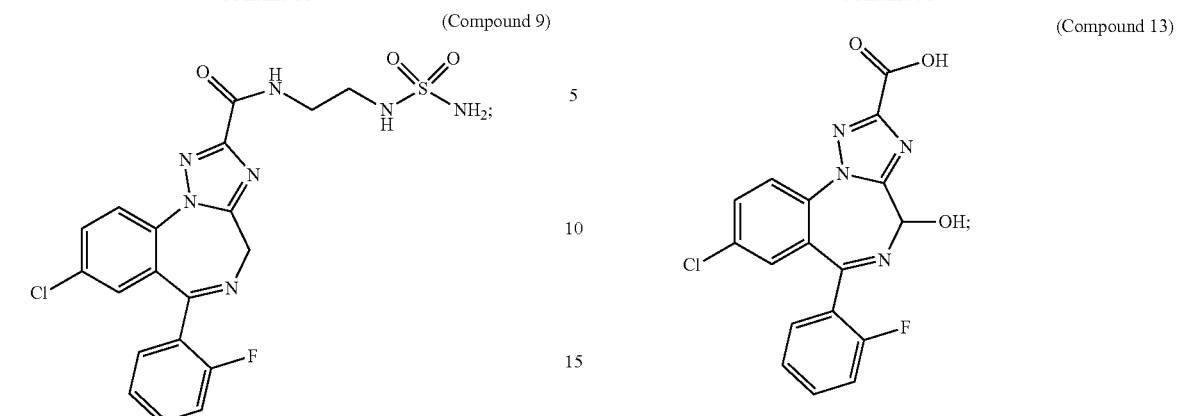
(Compound 10)
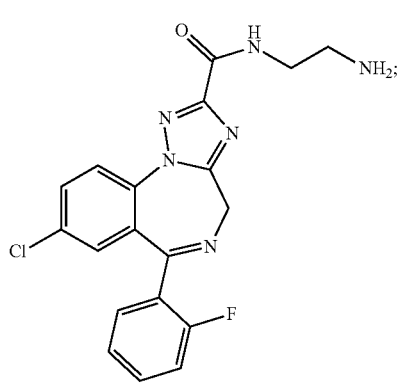
(Compound 11)
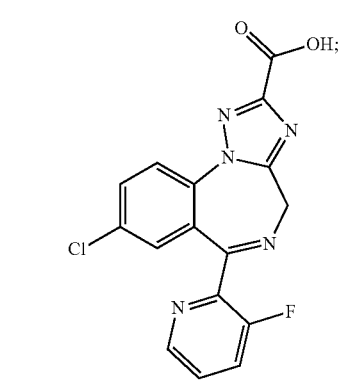
(Compound 12)
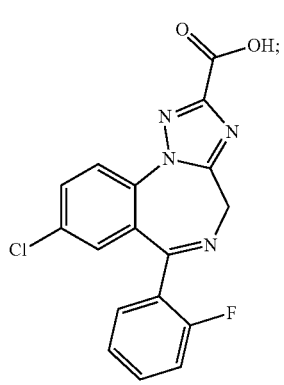
-continued
(Compound 13)
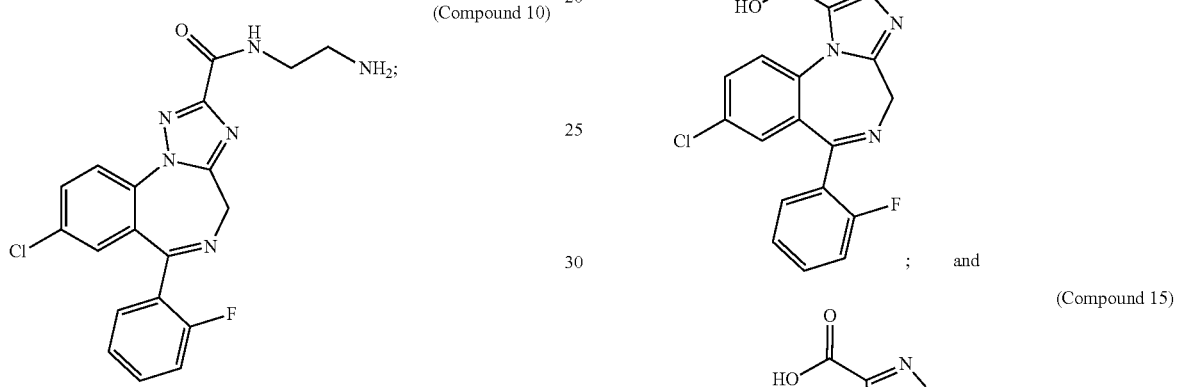
(Compound 14)
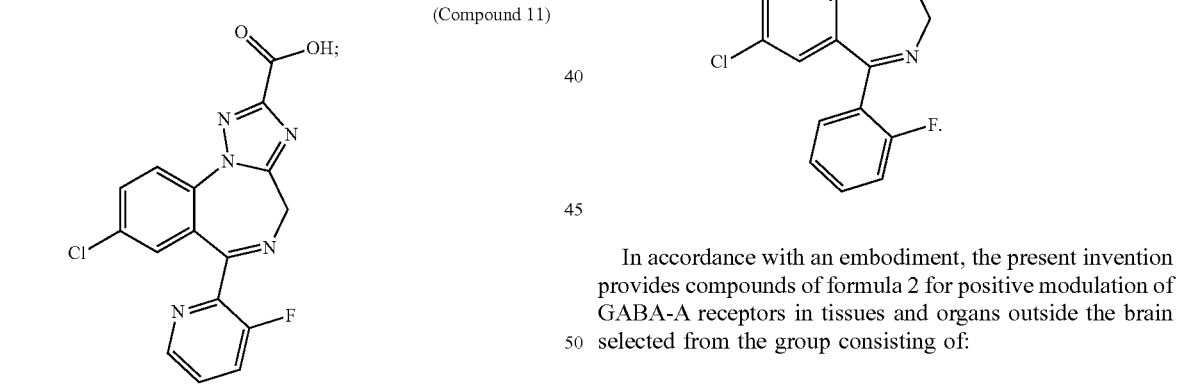
(Compound 15)
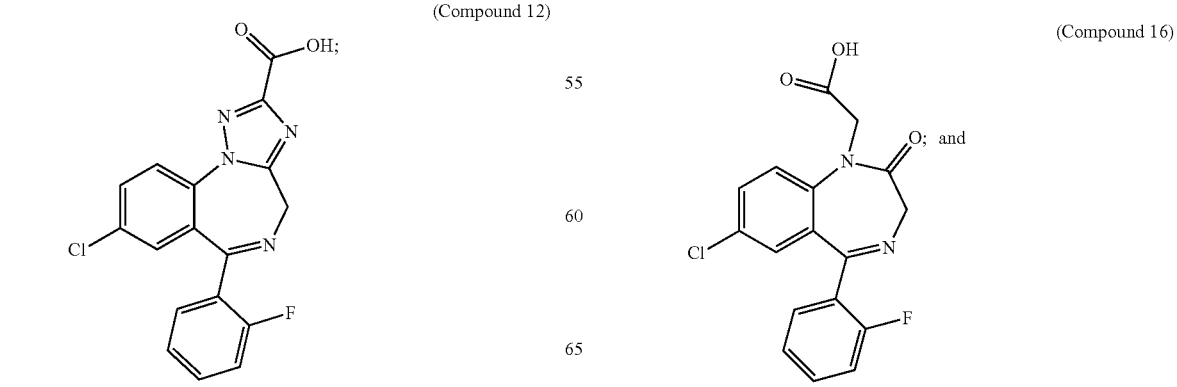
In accordance with an embodiment, the present invention provides compounds of formula 2 for positive modulation of GABA-A receptors in tissues and organs outside the brain selected from the group consisting of:
(Compound 16)

-continued

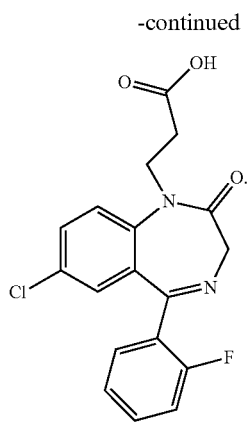

(Compound 17)

In accordance with another embodiment, the present invention provides pharmaceutical compositions comprising the compounds of formulas 1 or 2, as described herein, and a pharmaceutically acceptable carrier.

Definitions

As used herein, the chemical terms used above are standard chemical terminology. Sample definitions of such chemical substituents can be found in U.S. Pat. No. 8,530,438; which is incorporated herein by reference in its entirety.

As used herein, "peripherally restricted" or "restricted access to the central nervous system" generally refers to a compound that does not substantially cross an intact blood brain barrier of a subject. The term also encompasses compounds that may cross an intact blood brain barrier, but upon administration is rapidly metabolized to a form that does not substantially cross an intact blood brain barrier of the subject. A compound may be considered "peripherally restricted" if, upon administration to a subject, less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.5%, less than 0.1% of the compound crosses an intact blood brain barrier of the subject. In some embodiments, the term "peripherally restricted can mean that the concentration of a compound in the brain compared to the concentration in the circulating plasma (brain:plasma) ratio of about 1:5, preferably 1:10 or greater. In one exemplary embodiment the brain:plasma ratio is determined by measuring the ratio of a compound in mice or rats.

As used herein, the term "an effective amount" or "a therapeutically effective amount" refers to the amount of a compound that is sufficient to affect the intended application, including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "positive modulation" or "positive allosteric modulation" and all words stemming therefrom, refer to compounds that bind to an allosteric site on a receptor complex and affect it in a positive manner. Affecting a receptor in a positive manner typically means causing increased efficiency of the main receptor site. Increased receptor efficiency can mean potentially inducing a receptor to undergo a conformational change, or where the channel opens more frequently or for longer periods of time when an agonist binds to the receptor.

As used herein, "visceral pain" refers to pain that results from the activation of nociceptors of the thoracic, pelvic, or abdominal organs. Problems with organs, for example but not limited to, the stomach, kidney, gallbladder, urinary bladder, and intestines, can lead to visceral pain. Such problems can include distension, perforation, inflammation, impaction, and constipation. The visceral pain can be diffuse, vague, dull, deep, squeezing, pressure-like, and difficult to localize. The visceral pain may be accompanied by symptoms such as nausea, vomiting, sweating, and changes in blood pressure, heart rate, and temperature. Visceral pain can often be experienced, or "referred" to different sites of the body.

As used herein, "gut motility" refers to stretching and contractions of the muscles of the gastrointestinal tract. Peristaltic movement is the cyclical relaxation of circular smooth muscles, followed by their longitudinal contraction. Gut motility can be impaired, which can lead to abnormal contractions, including spasms and paralysis.

As used herein, "irritable bowel syndrome" or "IBS" generally refers to a syndrome in which subjects experience recurrent or chronic gastrointestinal symptoms. Symptoms of IBS can include, e.g., abdominal pain, abdominal discomfort, constipation, diarrhea, mucus in the stool, abdominal bloating, or a combination of any of the above. IBS may be diagnosed when a person has had abdominal pain or discomfort at least 3 times a month for the last 3 months without other disease or injury that could explain the pain. The pain or discomfort of IBS may occur with a change in stool frequency or consistency or be relieved by a bowel movement. IBS can be classified into four subtypes based on a subject's usual stool consistency. The four subtypes of IBS are: IBS with constipation (IBS-C), IBS with diarrhea (IBS-D), mixed IBS (IBS-M), and unsubtyped IBS (IBS-U). A subject with IBS-C may have hard or lumpy stools at least 25 percent of the time, may have loose or watery stools less than 25 percent of the time, or a combination of the two. A subject with IBS-D may have loose or watery stools at least 25 percent of the time, hard or lumpy stools less than 25 percent of the time, or a combination of the two. A subject with IBS-M may have hard or lumpy stools at least 25 percent of the time and loose or watery stools at least 25 percent of the time. A subject with IBS-U may have hard or lumpy stools less than 25 percent of the time, loose or watery stools less than 25 percent of the time, or a combination of the two. Constipation associated with IBS may be due to slow or delayed gastric motility. In some embodiments, the subject with IBS has experienced constipation. IBS can be diagnosed in a subject by any methods known in the art or otherwise described herein. For instance, IBS may be diagnosed by a health care provider. The health care provider may conduct a physical exam and may take a medical history of the subject. IBS may be diagnosed if a subject has exhibited one or more symptoms of IBS for at least 3, 4, 5, or 6 months, with one or more symptoms occurring at least three times a month for the previous 3 months. Additional tests that may be useful in the diagnosis of IBS include, but are not limited to: a stool test, lower GI series, flexible sigmoidoscopy, or colonoscopy.

The term "functional abdominal pain" or "functional abdominal pain syndrome" (FAPS) generally refers to a chronic and or frequently recurring pain not associated with changes in bowel movement patterns or with altered motility in the intestines. Normal abdominal activity may be experienced as being painful and contribute to functional abdominal pain. Functional abdominal pain may be related to central hypersensitivity, where the brain may fail to regulate pain signals from the gastrointestinal tract. While symptoms of FAPS can appear without apparent cause, they can also occur after infections or events that stimulate the bowel and also after traumatic life events like the death of a loved one, a divorce, or a history of sexual or physical abuse. During times of added stress, symptoms can worsen.

Repeated injury in the abdomen can cause nerve receptors to become overly sensitive. For instance, if someone has had multiple abdominal surgeries or an infection, a later painful occurrence may be experienced as more painful than previously. Even normal abdominal activity may be experienced as being painful. It is as if the volume has been turned up on a stereo receiver. This condition is called visceral hypersensitivity (i.e., increased sensitivity of the intestines). Furthermore although the brain has an ability to "turn down" the pain signals from the GI tract with FAPS, this ability is reduced, so even small amounts of intestinal disturbance can be amplified to produce severe pain (central hypersensitivity). So these individuals have an altered "braingut axis" where there is a failure of the brain to regulate even normal gut nerve activity leading to increased pain.

For purposes of the present invention, the term "diarrhea," as used herein means frequent, poorly formed, loose, watery stools of a subject. A subject having diarrhea means the subject is passing loose stools at least three times a day. The term "acute diarrhea" is a common problem that usually lasts <7 days but can last in a protracted or prolonged form for <21 days. Diarrhea lasting more than 2 days is often a sign of an enteropathogenic infection. The term "chronic diarrhea" means diarrhea that lasts at least 4 weeks. Chronic diarrhea symptoms may be continual or intermittent. The term "traveler's diarrhea" means diarrheal symptoms associated with travel-related infection. It may be caused by many different organisms, including bacteria such as *E. coli, Salmonella, Shigella, Campylobacter, Aeromonas, Plesiomonas*, and vibrios; parasites such as *Giardia, Entamoeba histolytica, Cryptosporidium*, and *Cyclospora*; and viruses. In addition to diarrhea, symptoms may include nausea, vomiting, abdominal pain, fever, sweats, chills, headache, and malaise. Diarrhea may also be the result of food borne enteropathogens. Typical food borne pathogens are *E. coli, Salmonella, Shigella, Yersinia*, and *Campylobacter*.

Diarrhea of any duration may cause dehydration, which means the body lacks enough fluid and electrolytes—chemicals in salts, including sodium, potassium, and chloride—to function properly. Loose stools contain more water and electrolytes and often weigh more than solid stools.

The term "functional idiopathic diarrhea" generally refers to diarrhea occurring for unknown reasons. Idiopathic diarrhea generally lasts for less than 5 days and often resolves within 2 or 3 days. Diarrhea generally means an increased frequency or decreased consistency of bowel movements. Diarrhea can also mean an increase in stool weight.

The term "inflammatory bowel diseases" generally refers to chronic inflammation of all or part of the gastrointestinal tract. Symptoms of inflammatory bowel diseases can involve severe diarrhea, pain, abdominal pain and cramping, blood in the subject's stool, fatigue, reduced appetite and weight loss, or a combination of any of the above. Additional symptoms of inflammatory diseases also include bowel obstruction, ulcers, perforated colon, fistulas, anal fissure, malnutrition, severe dehydration, increased risk of colon cancer. Non limiting examples of inflammatory bowel diseases include Crohn's disease and ulcerative colitis, which itself may have several different subtypes, such as ulcerative proctitis, proctosigmoiditis, left-sided colitis, pancolitis, acute severe ulcerative colitis. Inflammatory bowel disease can be diagnosed in a subject by any methods known in the art or otherwise described herein. For instance, inflammatory bowel disease may be diagnosed by a health care provider. A physician or health care provider may perform or order a combination of tests to confirm the presence of inflammatory bowel disease, including, but not limited to, blood tests of anemia or infection, fecal occult blood test, colonoscopy, flexible sigmoidoscopy, upper endoscopy, capsule endoscopy, double-balloon endoscopy, x-ray, computerized tomography scan, magnetic resonance imaging, or small bowel imaging.

The term "drug induced pain" is the unintended effect of a drug, which results in symptoms sufficient to prompt a patient to seek medical attention and/or require hospitalization. Examples of medications that are known to induce pain include: chemotherapy drugs, which are known to cause nerve damage in the form of peripheral neuropathy. In fact, the onset of peripheral neuropathy can be the primary limiting factor for the amount and duration of the chemotherapy; cholesterol-lowering drugs that people take medications to lower cholesterol levels are known to cause muscle pain and weakness is well known to be a resulting side-effect from cholesterol-lowering drugs; and opioids (hydrocodone, hydromorphone, oxycodone, morphine) when used for years and the pain becomes worse, this vicious pain cycle can be a result of opioid-induced hyperalgesia.

Proteins, carbohydrates, fats, and most fluids are absorbed in the small intestine (small bowel). Malabsorption syndrome occurs when something prevents the bowel from absorbing important nutrients and fluids. The problem may be caused by inflammation, disease, or injury. Sometimes, the condition may be the result of the body's failure to produce enzymes needed to digest some foods. Factors that may cause malabsorption syndrome include: antibiotic use; conditions such as celiac disease, chronic pancreatitis, cystic fibrosis, and dairy protein allergies; congenital (birth) defects or diseases of the gall bladder, liver, or pancreas; damage to the intestine (from infection, inflammation, injury, or surgery); and radiation therapy (which may injure the mucosal lining of the bowel). Symptoms can include bloating, flatulence, or explosive diarrhea.

The term "bile salt malabsorption" generally refers increased bile salts in the gastrointestinal tract, which can cause fluid to be pumped into the colon, causing diarrhea. Other symptoms of bile salt malabsorption can also include cramping in the abdomen, smelly wind, weight loss, gall stones, and kidney stones. There are currently three recognized types of bile salt malabsorption: (1) bile salt malabsorption, secondary to ileal resection, or ileal inflammation, (2) idiopathic/primary bile salt malabsorption, and (3) secondary to various gastrointestinal diseases. Bile salt malabsorption can be diagnosed in a subject by any methods known in the art or otherwise described herein. For instance, bile salt malabsorption may be diagnosed by a health care provider. A physician or health care provider may perform or order a combination of tests to confirm the presence of bile salt malabsorption, including, but not limited to, a SeHCAT scan, measurement of 7 alpha-hydroxy-4-cholesten-3-one, and fasting blood FGF19 values.

The terms "treat" and "prevent" as well as words stemming therefrom, as used herein, refer to an approach for obtaining beneficial or desired results including but not limited to a therapeutic benefit and/or a prophylactic benefit. A therapeutic benefit can mean eradication or amelioration of the underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying or eliminating the appearance of a disease or condition, delaying or eliminating the onset of symptoms of a disease or condition, slowing, halting, or reversing the progression of a disease or condition, or any combination thereof. For prophylactic benefit, the compositions may be administered to a subject at risk of developing a particular disease, or to a subject reporting one or more of the physiological symptoms of a disease, even though a diagnosis of this disease may not have been made. Therefore, there are varying degrees of treatment or prevention of which one of ordinary skill in the art recognizes as having a potential benefit or therapeutic effect. In this respect, the inventive methods can provide any amount of any level of treatment or prevention of a GABA-A mediated disease in a mammal. Furthermore, the treatment or prevention provided by the inventive method can include treatment or prevention of one or more conditions or symptoms of a disease, e.g., IBS, being treated or prevented.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human. In some cases, the subject in not an adult.

The term "alkyl," as used herein, refers to a hydrocarbon chain that is a straight chain or branched chain, containing the indicated number of carbon atoms. For example, $C_1$-$C_4$ alkyl group indicates that the group has from 1 to 4 (inclusive) carbon atoms in it. Similarly, $C_1$-$C_{10}$ alkyl group indicates that the group has from 1 to 10 (inclusive) carbon atoms in it. Unless stated otherwise specifically in the specification, an alkyl group is optionally substituted.

The term "alkenyl," as used herein, refers to a hydrocarbon chain that is a straight chain or branched chain, containing the indicated number of carbon atoms having one or more carbon-carbon double bonds. For example, $C_2$-$C_4$ alkenyl group indicates that the group has from 2 to 4 (inclusive) carbon atoms in it. Similarly, $C_2$-$C_{10}$ alkenyl group indicates that the group has from 2 to 10 (inclusive) carbon atoms in it. Unless stated otherwise specifically in the specification, an alkenyl group is optionally substituted.

The term "alkynyl," as used herein, refers to a hydrocarbon chain that is a straight chain or branched chain, containing the indicated number of carbon atoms having one or more carbon-carbon triple bonds. For example, $C_2$-$C_4$ alkynyl group indicates that the group has from 2 to 4 (inclusive) carbon atoms in it. Similarly, $C_2$-$C_{10}$ alkynyl group indicates that the group has from 2 to 10 (inclusive) carbon atoms in it. Unless stated otherwise specifically in the specification, an alkynyl group is optionally substituted.

The term "halo" or "halogen," as used herein, refers to fluoro, chloro, bromo, or iodo.

The term "cycloalkyl" or "carbocyclic ring", as used herein, refers to a stable non-aromatic monocyclic or polycyclic hydrocarbon radical consisting solely of carbon and hydrogen atoms, which may include fused or bridged ring systems, having from three to fifteen carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. A "cycloalkenyl" is a cycloalkyl comprising one or more carbon-carbon double bonds within the ring. Unless otherwise stated specifically in the specification, a cycloalkyl (or cycloalkenyl) group is optionally substituted.

The term "heterocycloalkyl" or "heterocyclic ring" refers to a substituted or unsubstituted 3-, 4-, 5-, 6- or 7-membered saturated or partially unsaturated ring containing one, two, or three heteroatoms, independently selected from oxygen, nitrogen and sulfur; heterocycloalkyl may be unsubstituted or substituted with one or more substituents. The heterocycloalkyl may be optionally fused to another cycloalkyl, heterocycloalkyl, or an aryl. For example, to a benzo group.

The term "aryl", as used herein, refers to a hydrocarbon ring system radical comprising, e.g., 6 to 18 carbon atoms and at least one aromatic ring. The aryl radical can be a monocyclic, bicyclic, tricyclic, or tetracyclic ring system, which may include fused or bridged ring systems. Aryl radicals can include, but not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

The term "Heteroaryl", as used herein, refers to a 5- to 14-membered ring system radical comprising one or more heteroatoms selected from the group consisting of nitrogen, oxygen, and sulfur. The heteroaryl radical may be a monocyclic, bicyclic, tricyclic, or tetracyclic ring system, which may include fused or bridged ring systems; the nitrogen, carbon or sulfur atoms in the heteroaryl radical may be optionally oxidized; and the nitrogen atom may be optionally quaternized. Exemplary heteroaryl groups may include, but not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

Exemplary Pharmaceutical Compositions

Accordingly, included within the compounds of the present invention are the tautomeric forms of the disclosed compounds, isomeric forms including enantiomers, stereoisomers, and diastereoisomers, and the pharmaceutically-acceptable salts thereof.

The salts of the compounds of formulas 1 or 2 used in the method of treatment described herein will be pharmaceutically acceptable salts. A person of ordinary skill in the art would recognize that non-pharmaceutically acceptable salts may be used as intermediaries in the preparation of the compounds of formula I or its derivatives and their pharmaceutically acceptable salts. When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids. In a further embodiment of the present invention, a formulation comprising a compound of formulas 1 and 2, or a salt, solvate, or stereoisomer thereof, and a suitable pharmaceutically acceptable carrier is provided as understood by a person of ordinary skill in the art.

In yet a further aspect of the present invention, a method for treating a patient with IBS is provided. The method comprises the steps of administering one or more compounds of formulas 1 and 2, or a salt, solvate, or stereoisomer thereof, or a derivative thereof to a subject. The compounds can be provided with a pharmaceutically acceptable carrier, when necessary.

Carriers and Excipients

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), antioxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

In some embodiments, the pharmaceutically acceptable carrier comprises more than 90%, more than 80%, more than 70%, more than 60%, more than 50%, more than 40%, more than 30%, more than 20%, more than 10%, more than 9%, more than 8%, more than 6%, more than 5%, more than 4%, more than 3%, more than 2%, more than 1%, more than 0.5%, more than 0.4%, more than 0.3%, more than 0.2%, more than 0.1%, more than 0.09%, more than 0.08%, more than 0.07%, more than 0.06%, more than 0.05%, more than 0.04%, more than 0.03%, more than 0.02%, more than 0.01%, more than 0.009%, more than 0.008%, more than 0.007%, more than 0.006%, more than 0.005%, more than 0.004%, more than 0.003%, more than 0.002%, more than 0.001%, more than 0.0009%, more than 0.0008%, more than 0.0007%, more than 0.0006%, more than 0.0005%, more than 0.0004%, more than 0.0003%, more than 0.0002%, or more than 0.0001% of the pharmaceutical composition by w/w, w/v or v/v.

In some embodiments, the concentration of the compound in the composition comprises less than 100%, less than 90%, less than 80%, less than 70%, less than 60%, less than 50%, less than 40%, less than 30%, less than 20%, less than 10%, less than 9%, less than 8%, less than 6%, less than 5%, less than 4%, less than 3%, less than 2%, less than 1%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, less than 0.01%, less than 0.009%, less than 0.008%, less than 0.007%, less than 0.006%, less than 0.005%, less than 0.004%, less than 0.003%, less than 0.002%, less than 0.001%, less than 0.0009%, less than 0.0008%, less than 0.0007%, less than 0.0006%, less than 0.0005%, less than 0.0004%, less than 0.0003%, less than 0.0002%, or less than 0.0001% of the pharmaceutical composition by w/w, w/v or v/v.

In some embodiments, the concentration of the compound is in the range of about 0.0001% to about 50%, about 0.001% to about 40%, about 0.01% to about 20%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% of the pharmaceutical composition by w/w, w/v or v/v.

In some embodiments, the concentration of the compound is in the range of about 0.0001% to about 5%, about 0.001% to about 4%, about 0.01% to about 2%, about 0.02% to about 1%, or about 0.05% to about 0.5% of the pharmaceutical composition by w/w, w/v or v/v.

In some embodiments, the amount of the compound in the pharmaceutical composition is about 0.00001 mg, 0.0001 mg, 0.001 mg, 0.005 mg, 0.01 mg, 0.05 mg, 0.1 mg, 0.25 mg, 0.5 mg, 1 mg, 2 mg, 4 mg, 8 mg, 10 mg, 12 mg, 14 mg, 16 mg, 18 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 1.1 g, 1.2 g, 1.3 g, 1.4 g, 1.5 g, 1.6 g, 1.7 g, 1.8 g, 1.9 g, 2 g, 2.5 g, 3 g, 3.5 g, 4 g, 4.5 g, 5 g, 6 g, 7 g, 8 g, 9 g, or 10 g.

Exemplary Modes of Administration

Administration of a pharmaceutical composition as described herein can be performed by any method that enables delivery of the compound to the site of action. The composition may be administered orally, parenterally, enterally, intraperitoneally, topically, transdermally, ophthalmically, intranasally, locally, non-orally, via spray, subcutaneously, intravenously, intratonsillary, intramuscularly, buccally, sublingually, rectally, intra-arterially, by infusion, or intrathecally. In some embodiments, the composition is administered orally. In some cases, the oral administration may comprise administration of any of the oral dosage forms as described herein. In some cases, a composition described herein is administered sublingually. In some cases, a composition described herein is administered transdermally, e.g., via transdermal patch. The effective amount of a compound administered will be dependent on the subject being treated, the severity of the disorder or condition, the rate of administration, the disposition of the compound and the discretion of the prescribing physician.

Pharmaceutical Compositions for Oral Administration

The pharmaceutical composition comprising an effective amount of a compound can be formulated for oral administration. In some embodiments, the pharmaceutical composition comprising an effective amount of a compound for oral administration is a solid pharmaceutical composition. In some embodiments, the solid pharmaceutical composition may be presented as discrete (e.g., unit) oral dosage forms. Non-limiting examples of discrete oral dosage forms include tablets, capsules, caplets, gelatin capsules, sustained release formulations, lozenges, thin films, lollipops, chewing gum. In some embodiments, the discrete oral dosage form is an orally disintegrating oral dosage form, such as, an orally disintegrating tablet.

In some embodiments, the pharmaceutical composition comprising an effective amount of a compound for oral administration is a liquid pharmaceutical composition. Non-limiting examples of liquid compositions for oral administration include hydrophilic suspensions, emulsions, liquids, gels, syrups, slurries, solutions, elixirs, softgels, tinctures, and hydrogels. In some embodiments, solid or liquid compositions comprising an effective amount of a compound for oral administration comprise various sweetening or flavoring agents, or coloring agents. Examples of coloring agents include dyes suitable for food such as those known as F.D. & C. dyes and natural coloring agents such as grape skin extract, beet red powder, beta carotene, annato, carmine, turmeric, paprika, and so forth. Derivatives, analogues, and isomers of any of the above colored compound also may be used. The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Pharmaceutical Compositions for Injection or Parenteral Administration

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

Other Pharmaceutical Compositions

Alternatively, the compounds of the present invention can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous or non-porous material, such as a polymer, wherein the compound is encapsulated by or diffused throughout the material and/or degradation of the non-porous material. The depot is then implanted into the desired location within the body and the compounds are released from the implant at a predetermined rate.

In one embodiment, the compounds of the present invention provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all or substantially all of the compound is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

In an embodiment, the pharmaceutical compositions of the present invention comprise the compounds of the present invention, for example, the compounds disclosed herein, and/or their salts, solvates or stereoisomers thereof, and optionally, one or more additional therapeutic agents, such as, for example, 5-HT receptor inhibitors, antibiotics, anti-inflammatory, immunomodulators, together with a pharmaceutically acceptable carrier.

Examples of antibiotic agents suitable for use in pharmaceutical composition comprising the compounds heretofore described above and one or more antibiotic agents include, for example, quinolone antibiotics, such as levofloxacin, ciprofloxacin, ibafloxacin, pradofloxacin, rosoxacin, and sarafloxacin. Other suitable antibiotics are trimethoprim-sulfamethoxazole mixtures such as Bactrim®. Alternatives include rifaximin and azithromycin. Dosages vary with the weight and age of the subject to be treated. Typically, quinolone antibiotics and trimethoprim-sulfamethoxazole mixtures are given at dosages between 250 and 500 mg daily. For trimethoprim-sulfamethoxazole, the dosages are generally between about 5 mg/kg and 25 mg/kg. For rifaximin the dosage ranges from 100 mg to about 500 mg, with 200 mg being preferred. Azithromycin is typically administered at 250-500 mg/day. The dosages required are well within the knowledge of those of ordinary skill in the art.

General Considerations

For purposes of the invention, the amount or dose of the compounds, salts, solvates, or stereoisomers of any one the compounds of Formula I, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of any one the compounds as set forth above, of the present invention also will be determined by the existence, nature and extent of any adverse side effects that might accompany the administration of a particular compound.

Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 100 mg/kg body weight/day, about 0.1 mg to about 10 mg/kg body weight/day. The several aspects of the present invention, described above, are shown in the following examples.

EXAMPLES

Example 1. 8-Chloro-6-(2-fluorophenyl)-4H-[1,2,4]triazolo[1,5-a][1,4]benzodiazepine-2-carboxylic acid

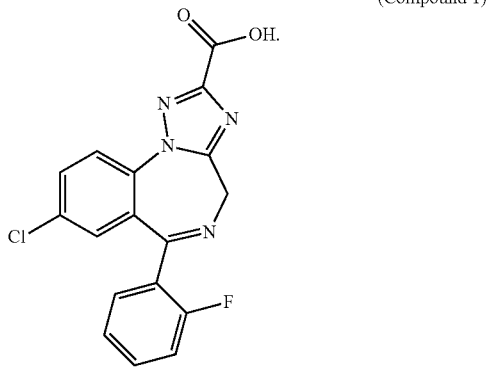

(Compound 1)

Step 1: Diethyl 2-[(2-chloroacetyl)amino]propanedioate

To a stirring mixture of diethyl 2-aminopropanedioate hydrochloride (10 g, 47.25 mmol) and chloroacetyl chloride (5.33 g, 47.25 mmol) in 1,2-dichloroethane (120 ml) at 0° C., Triethylamine (19.65 ml, 141.75 mmol) was added slowly into the solution. The solution was heated to its boiling point for 10 min., then it was cooled to room temperature and stirred at room temperature overnight. The solution was diluted with dichloromethane (100 ml). The solution was filtered to remove the triethyl amine hydrochloride salt. The filtrate was extracted with HCl solution (1 N, 2×30 ml), water (1×50 ml) and brine (1×50 mL), dried over sodium sulfate. The solution was filtered and concentrated. The residue was recrystallized in cyclohexane to give the title compound as slightly colored solid (7.2 g, 61%) (Kitagawa, Nakamura, Masai, "Synthesis and Root Growth-Inhibitory Activity of 2- and 3-(Haloacetylamino)-1-(2furyl) propanoic Acids" Chem. Pharm. Bull., 51(8) 994-998 (2003). MS (ES+) m/z 252.0 [M+H]$^+$. 1H NMR (400 MHz, CHLOROFORM-d) δ ppm 1.28-1.39 (m, 6H) 4.10-4.17 (m, 2H) 4.24-4.39 (m, 4H) 5.16 (d, J=6.82 Hz, 1H)

Step 2: Diethyl 2-[(2-chloroacetyl)amino]-2-[(E)-[4-chloro-2-(2-fluorobenzoyl)phenyl]azo]propanedioate To a stirring solution of (2-amino-5-chloro-phenyl)-(2-fluorophenyl)methanone (6.94 g, 27.8 mmol) in acetic acid (26 ml) with stirring at room temperature, concentrated hydrochloric acid (6.95 ml, 83.4 mmol) was added. Sodium nitrite (5 M) solution (5.56 ml, 27.81 mmol) was added. The solution was stirred at room temperature for 15 min. Ice (19 g) was added. The solution of diethyl 2-[(2-chloroacetyl)amino]propanedioate (7.0 g, 27.8 mmol) dissolved in acetone (60 ml) was added dropwise quickly. The solution was cooled to 0° C. Saturated potassium carbonate solution (4.2 ml) was added. The pH of the solution was between 5 and 6.5. The solution was stirred at room temperature for 1 hr. The solution was extracted with ethyl acetate (2×70 ml). The combined organic solution was washed with water (35 ml) and brine (35 ml), dried over sodium sulfate. The solution was filtered and concentrated. The residue was purified over ISCO eluted with ethyl acetate/hexane (0-30%) to give the title compound as deep colored oil (10.8 g, 76%). MS (ES+) m/z 534.0 [M+Na]$^+$. 1H NMR (400 MHz, CHLOROFORM-d) δ ppm 1.24-1.36 (m, 6H), 3.87 (s, 2H), 4.21-4.36 (m, 4H), 7.49-7.80 (m, 7H)

Step 3: 1-[4-chloro-2-(2-fluorobenzoyl)phenyl]-5-(chloromethyl)-1,2,4-triazole-3-carboxylic acid To a stirring solution of diethyl 2-[(2-chloroacetyl)amino]-2-[(E)-[4-chloro-2-(2-fluorobenzoyl)phenyl]azo] propanedioate (1.33 g, 2.5 mmol) in methanol (20 ml), sodium hydroxde solution (1 N, 7.8 ml, 7.8 mmol) was added. The solution was stirred at room temperature for 4 hrs. The product was precipitated by adding 10% HCl solution to adjust the solution to acidic. The solution was extracted with dichloromethane (3×50 ml). The combined DCM solution was washed with brine, dried over sodium sulfate. The solution was filtered and concentrated. The residue was recrystallized in dichloromethane/hexane to give the title compound as white solid (0.86 g, 84%). MS (ES+) m/z 394.0 [M+H]$^+$1H NMR (400 MHz, DMSO-d6) δ ppm 4.87 (s, 2H), 7.15-7.26 (m, 2H) 7.49 (td, J=7.52, 1.89 Hz, 1H) 7.55-7.66 (m, 1H) 7.83-7.94 (m, 2H) 8.00 (dd, J=8.46, 2.40 Hz, 1H)

Step 4: 8-Chloro-6-(2-fluorophenyl)-4H-[1,2,4]triazolo[1,5-a][1,4]benzodiazepine-2-carboxylic acid To a stirring solution of ammonia in methanol (7 N, 5 ml) at 0° C., 1-[4-chloro-2-(2-fluorobenzoyl)phenyl]-5-(chloromethyl)-1,2,4-triazole-3-carboxylic acid (0.180 mg, 0.46 mmol) in methanol (2 ml) was added. Potassium iodide (4 mg) was also added. The solution was stirred at room temperature for three days. The solution was concentrated. The residue was purified over ISCO eluted with methanol (10% acetic acid)/DCM (0-40%). The residue from ISCO purification was washed with diethyl ether to give the title compound as purple solid (100 mg, 61%). MS (ES+) m/z 357.0 [M+H]$^+$ 1H NMR (400 MHz, DMSO-d6) δ ppm 13.76 (br. s., 1H), 7.95-8.06 (m, 1H), 7.91 (dd, J=8.8, 2.3 Hz, 1H), 7.51-7.67 (m, 2H), 7.33-7.39 (m, 2H), 7.17-7.29 (m, 1H), 4.85 (br s, 2H).

Example 2. 6-(2-Fluorophenyl)-8-(trifluoromethyl)-4H-[1,2,4]triazolo[1,5-a][1,4]benzodiazepine-2-carboxylic acid

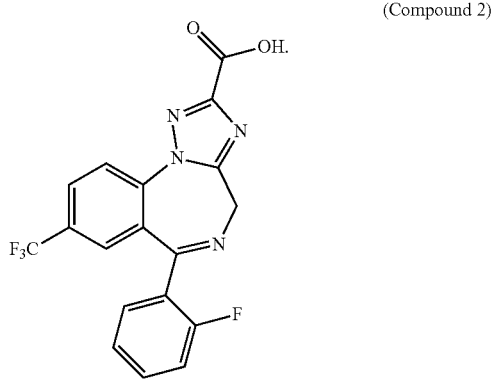 [SMILES: O=C(O)c1nc2n(n1)-c1ccc(C(F)(F)F)cc1C(c1ccccc1F)=NC2]

(Compound 2)

Step 1: Diethyl 2-[(2-chloroacetyl)amino]-2-[(E)-[2-(2-fluorobenzoyl)-4-(trifluoromethyl)phenyl]azo]propanedioate To a stirring solution of [2-amino-5-(trifluoromethyl)phenyl]-(2-fluorophenyl)methanone (500. mg, 1.77 mmol) in acetic acid (10 mL) at 0° C., hydrochloric acid (Concentrated) (0.44 mL, 5.3 mmol) was added. Sodium nitrite (0.35 mL, 1.77 mmol) was also added. The solution was stirred at 0° C. for 15 min. Ice (0.4 g) was added. The solution of diethyl 2-[(2-chloroacetyl)amino]propanedioate (444.28 mg, 1.77 mmol) in acetone (10 mL) was added dropwise quickly. Potassium carbonate (saturated solution) (0.6 mL, 1.77 mmol) was added. The pH of the solution was between 5 and 6.5. The solution was stirred at room temperature for 1 hour. The solution was extracted with ethyl acetate (2×20 ml). The combined organic solution was washed with water (1 ml) and brine (1 ml), dried over sodium sulfate. The solution was filtered and concentrated. The residue was purified by silica gel chromatography eluted with ethyl acetate/hexane (0-50%) to give the title compound (0.9500 g) as deep colored oil. MS (ES+) m/z 568.0 [M+Na]+. 1H NMR (CHLOROFORM-d) δ: 7.77-7.88 (m, 2H), 7.56-7.71 (m, 1H), 7.29-7.35 (m, 1H), 7.09 (ddd, J=10.9, 8.3, 1.0 Hz, 3H), 4.23-4.40 (m, 4H), 4.10-4.17 (m, 1H), 3.88 (s, 1H), 2.09-2.14 (m, 5H), 2.04-2.09 (m, 2H), 1.24-1.33 (m, 6H).

Step 2: 5-(chloromethyl)-1-[2-(2-fluorobenzoyl)-4-(trifluoromethyl)phenyl]-1,2,4-triazole-3-carboxylic acid To a stirring solution of diethyl 2-[(2-chloroacetyl)amino]-2-[(E)-[2-(2-fluorobenzoyl)-4-(trifluoromethyl)phenyl]azo]propanedioate (0.76 g, 1.4 mmol) in methanol (40 mL), potassium carbonate (0.97 g, 7 mmol) dissolved in water (5 mL) was added. The solution was stirred at room temperature for 4 hrs. The solution was adjusted to acidic by adding hydrochloric acid (1.0 N, 20 ml). The solution was concentrated. The residue was dissolved in water (50 ml). The solution was extracted with ethyl acetate (2×50 ml). The combined organic solution was extracted with water (50 ml) and brine (50 ml), and dried over sodium sulfate. The solution was filtered and concentrated to give the title compound (590 mg) as deep colored oil. MS (ES+) m/z 428.0 [M+H]+ 1H NMR (CHLOROFORM-d) δ: 8.00-8.08 (m, 2H), 7.87 (d, J=8.1 Hz, 1H), 7.65 (td, J=7.6, 1.8 Hz, 1H), 7.21-7.27 (m, 1H), 7.06 (dd, J=10.7, 8.5 Hz, 1H), 4.71 (s, 2H)

Step 3: 6-(2-Fluorophenyl)-8-(trifluoromethyl)-4H-[1,2,4]triazolo[1,5-a][1,4]benzodiazepine-2-carboxylic acid To a stirring solution of 5-(chloromethyl)-1-[2-(2-fluorobenzoyl)-4-(trifluoromethyl)phenyl]-1,2,4-triazole-3-carboxylic acid (590 mg, 1.38 mmol) in ammonia methanol (11 mL, 77 mmol) mixture at 0° C., potassium iodide (50. mg, 0.3000 mmol) was added. The solution was stirred at room temperature for three days. The solution was concentrated. The residue was purified by preparative reverse-phase chromatography to give the title compound (34 mg) as white solid. MS (ES+) m/z 391.0 [M+H]+. 1H NMR (DMSO-d6) δ: 8.19-8.27 (m, 2H), 7.64-7.72 (m, 2H), 7.54-7.62 (m, 1H), 7.36 (td, J=7.6, 1.0 Hz, 1H), 7.24 (dd, J=11.1, 8.3 Hz, 1H), 4.97 (br. s., 2H).

Example 3. 8-Fluoro-6-(2-fluorophenyl)-4H-[1,2,4]triazolo[1,5-a][1,4]benzodiazepine-2-carboxylic acid

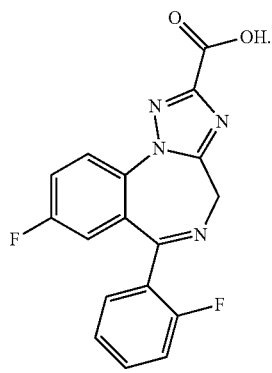

(Compound 3)

Following the procedure for example 1 except starting with (2-amino-5-fluoro-phenyl)-(2-fluorophenyl)methanone afforded 8-Fluoro-6-(2-fluorophenyl)-4H-[1,2,4]triazolo[1,5-a][1,4]benzodiazepine-2-carboxylic acid as a solid. 1H NMR (400 MHz, DMSO-d6) δ ppm 8.03 (dd, J=8.72, 4.93 Hz, 1H) 7.71 (td, J=8.46, 2.78 Hz, 1H) 7.52-7.65 (m, 2H) 7.34 (td, J=7.3, 1.3 Hz, 1H) 7.23 (dd, J=8.3, 9.4 Hz, 1H); 7.18 (dd, J=9.1, 2.8 1H); 4.88 (br s, 2H).

Example 4: 8-Bromo-6-(2-fluorophenyl)-4H-[1,2,4]triazolo[1,5-a][1,4]benzodiazepine-2-carboxylic acid

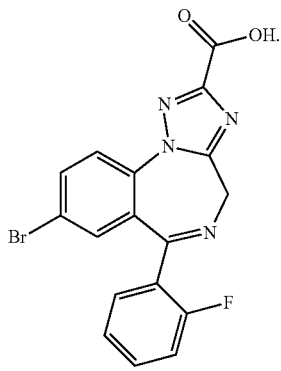

(Compound 4)

Following the procedure for example 1 except starting with (2-amino-5-bromo-phenyl)-(2-fluorophenyl)methanone afforded 8-Bromo-6-(2-fluorophenyl)-4H-[1,2,4]triazolo[1,5-a][1,4]benzodiazepine-2-carboxylic acid as a solid. MS (ES+) m/z 400.9 [M+H, Br=81]$^+$ 1H NMR (DMSO-d6) δ: 7.98-8.08 (m, 1H), 7.89-7.97 (m, 1H), 7.54-7.68 (m, 2H), 7.50 (d, J=2.0 Hz, 1H), 7.31-7.41 (m, 1H), 7.19-7.31 (m, 1H), 4.92 (br. s., 1H).

Example 5: 8-Chloro-6-(2,6-difluorophenyl)-4H-[1,2,4]triazolo[1,5-a][1,4]benzodiazepine-2-carboxylic acid

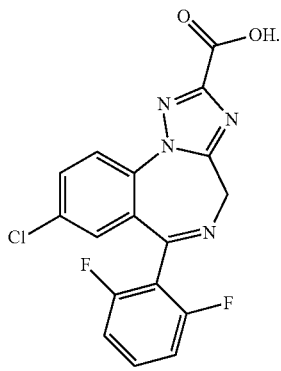

(Compound 5)

Following the procedure for example 1 except starting with (2-amino-5-chloro-phenyl)-(2,6-difluorophenyl)methanone afforded 8-chloro-6-(2,6-difluorophenyl)-4H-[1,2,4]triazolo[1,5-a][1,4]benzodiazepine-2-carboxylic acid as a solid. MS (ES+) m/z 375 [M+H]$^+$ 1H NMR (DMSO-d6) δ: 7.99-8.07 (m, 1H), 7.92 (dd, J=8.7, 2.4 Hz, 1H), 7.55-7.66 (m, 1H), 7.47 (d, J=2.3 Hz, 1H), 7.22 (t, J=8.5 Hz, 2H), 5.02 (s, 2H)

Example 6: 8-chloro-6-(2-fluorophenyl)-N-(2-ureidoethyl)-4H-[1,2,4]triazolo[1,5-a][1,4]benzodiazepine-2-carboxamide

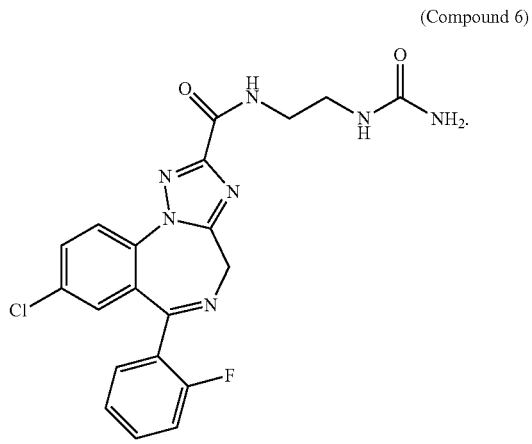 [SMILES: NC(=O)NCCNC(=O)c1nc2n(n1)-c1ccc(Cl)cc1C(c1ccccc1F)=NC2]

(Compound 6)

To a stirring mixture of 8-chloro-6-(2-fluorophenyl)-4H-[1,2,4]triazolo[1,5-a][1,4]benzodiazepine-2-carboxylic acid (100 mg, 0.2800 mmol) and 2-aminoethylurea hydrochloride (58.69 mg, 0.4200 mmol) in DMF (1.5 mL) was added N,N-diisopropylethylamine (108.68 mg, 0.8400 mmol) and HBTU (127.57 mg, 0.3400 mmol). The solution was stirred at room temperature for two days. The solution was directly purified by reverse-phase preparative HPLC (C18 column, 150×20 mm I.D., 5 μm particle size, gradient elution 5% CH$_3$CN/H$_2$O w. 0.05% TFA modifier to 95% CH$_3$CN/H$_2$O w. 0.05% TFA modifier) to give the title compound as white solid. $^1$H NMR (DMSO-d6) δ: 8.76-8.83 (m, 4H), 8.02 (d, J=8.8 Hz, 1H), 7.88-7.96 (m, 1H), 7.54-7.67 (m, 2H), 7.31-7.41 (m, 2H), 7.19-7.29 (m, 1H), 3.97 (s, 2H), 3.25-3.35 (m, 2H), 3.17 (s, 4H).

Example 7: 8-chloro-N-[2-(dimethylamino)ethyl]-6-(2-fluorophenyl)-4H-[1,2,4]triazolo[1,5-a][1,4]benzodiazepine-2-carboxamide

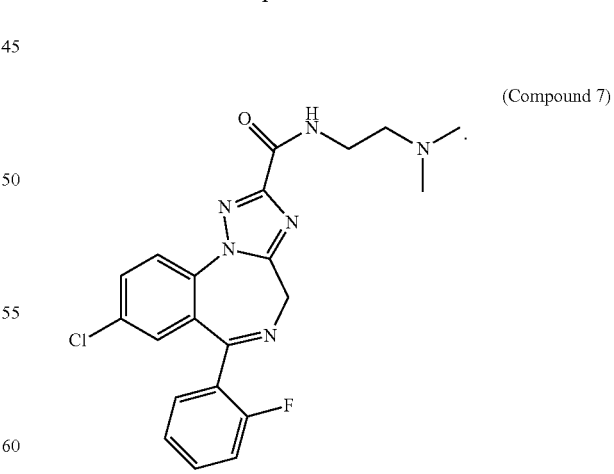

(Compound 7)

Following the procedure for example 6 except starting with N,N-dimethyl aminoethylamine afforded the title compound. MS (ES+) m/z 427.1 [M+H]$^+$ 1H NMR (400 MHz, DMSO-d6) δ ppm: 9.34 (br. s., 1H), 8.98-9.08 (m, 1H), 7.98-8.08 (m, 1H), 7.90-7.97 (m, 1H), 7.54-7.69 (m, 2H), 7.32-7.47 (m, 2H), 7.19-7.30 (m, 1H), 4.94 (br. s., 2H), 3.63 (q, J=5.81 Hz, 2H), 3.28 (d, J=5.81 Hz, 2H), 2.76-2.95 (m, 6H).

Example 8: 2-[[8-chloro-6-(2-fluorophenyl)-4H-[1,2,4]triazolo[1,5-a][1,4]benzodiazepine-2-carbonyl]amino]ethyl-trimethyl-ammonium trifluoroacetate

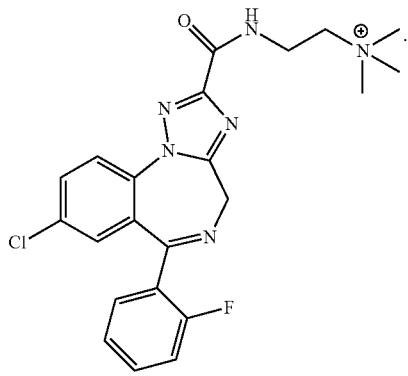

(Compound 8)

Following the procedure for example 6 except starting with N,N,N-trimethyl aminoethylammonium chloride afforded the title compound. MS (ES+) m/z 441.0 [M+]+ 1H NMR (400 MHz, DMSO-d6) δ ppm: 9.17 (t, J=5.94 Hz, 1H), 8.69 (br. s., 1H), 7.98-8.07 (m, 1H), 7.90-7.97 (m, 1H), 7.54-7.67 (m, 2H), 7.32-7.43 (m, 2H), 7.19-7.31 (m, 1H), 4.94 (br. s., 2H), 3.71 (d, J=6.57 Hz, 2H), 3.48-3.57 (m, 2H), 3.05-3.19 (m, 9H).

Example 9: 8-chloro-6-(2-fluorophenyl)-N-[2-(sulfamoylamino)ethyl]-4H-[1,2,4]triazolo[1,5-a][1,4]benzodiazepine-2-carboxamide

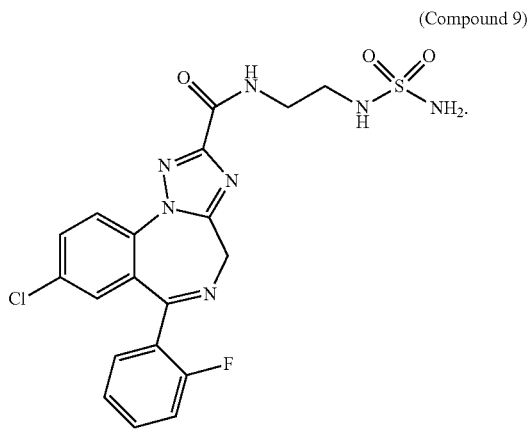 [SMILES: NS(=O)(=O)NCCNC(=O)c1nc2n(n1)-c1ccc(Cl)cc1C(c1ccccc1F)=NC2]

(Compound 9)

Following the procedure for example 6 except starting with 2-(sulfamoylamino)ethylamine afforded the title compound. MS (ES+) m/z 513.1 [M+H]+ 1H NMR (400 MHz, DMSO-d6) δ ppm 1.13-1.26 (m, 7H) 1.99 (s, 1H) 2.86-2.95 (m, 7H) 2.98-3.08 (m, 2H) 3.28-3.48 (m, 32H) 4.03 (q, J=7.07 Hz, 2H) 4.57 (s, 1H) 4.92 (br. s., 4H) 7.24 (dd, J=10.74, 8.46 Hz, 3H) 7.31-7.42 (m, 7H) 7.53-7.68 (m, 2H) 7.89-7.96 (m, 3H) 7.98-8.08 (m, 1H) 8.92 (q, J=5.64 Hz, 2H).

Example 10: N-(2-aminoethyl)-8-chloro-6-(2-fluorophenyl)-4H-[1,2,4]triazolo[1,5-a][1,4]benzodiazepine-2-carboxamide

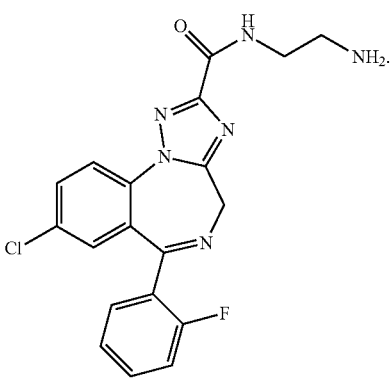

(Compound 10)

Following the procedure for example 6 except starting with excess ethylenediamine afforded the title compound. 1H NMR (400 MHz, DMSO-d6) δ ppm 2.67 (t, J=6.19 Hz, 2H) 3.26 (q, J=6.48 Hz, 16H) 4.92 (br. s., 9H) 7.24 (dd, J=10.48, 8.46 Hz, 8H) 7.31-7.42 (m, 15H) 7.52-7.67 (m, 16H) 7.88-7.96 (m, 7H) 7.99-8.09 (m, 8H) 8.69 (t, J=5.56 Hz, 6H).

Example 11: 8-Chloro-6-(3-fluoro-2-pyridyl)-4H-[1,2,4]triazolo[1,5-a][1,4]benzodiazepine-2-carboxylic acid

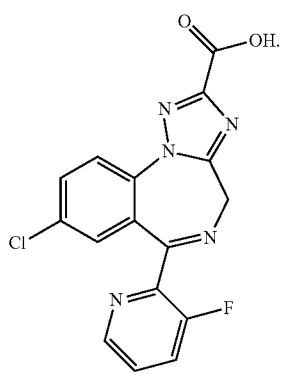

(Compound 11)

Step 1: Benzyl N-(2-chloro-2-oxo-ethyl)carbamate

To a stirring solution of Z-GLY-OH (5. g, 23.9 mmol) in dichloromethane (100 mL) at room temperature, oxalyl chloride (2.26 mL, 26.29 mmol) was added. DMF (three drops) was added afterward. The solution was stirred at room temperature for 5 hours. The solution was concentrated. The residue was used directly in the next reaction.

Step 2: Diethyl 2-[[2-(benzyloxycarbonylamino)acetyl]amino]propanedioate

To a stirring solution of benzyl N-(2-chloro-2-oxo-ethyl)carbamate (5.44 g, 23.9 mmol) and diethyl-2-aminomalonate (5.0 g, 23.9 mmol) in dichloromethane (100 mL) at 0° C., triethylamine (9.94 mL, 71.7 mmol) was added slowly into the solution. The solution was then heated under reflux for 20 min, then stirred at room temperature overnight. Dichloromethane (100 ml) was added. The solution was extracted with hydrochloric acid (1 N, 2×100 ml), water (100 mml, brine (100 ml), dried over sodium sulfate. The solution was filtered and concentrated. The residue was purified by silica gel chromatography eluted with ethyl acetate/hexanes (0-70%) to give the title compound (5.392 g) as white solid. MS (ES+) m/z 367.1 [M+H]⁺. 1H NMR (CHLOROFORM-d) δ: 7.30-7.41 (m, 5H), 5.12-5.20 (m, 3H), 4.21-4.35 (m, 4H), 4.00 (d, J=5.6 Hz, 2H), 1.26-1.36 (m, 6H).

Step 3: Diethyl 2-[[2-(benzyloxycarbonylamino)acetyl]amino]-2-[(E)-[4-chloro-2-(3-fluoropyridine-2-carbonyl)phenyl]azo]propanedioate To a stirring solution of (2-amino-5-chloro-phenyl)-(3-fluoro-2-pyridyl)methanone (500. mg, 1.99 mmol) in acetic acid (10 mL) at room temperature, hydrochloric acid (Concentrated) (0.5 mL, 5.98 mmol) was added. Sodium nitrite (0.4 mL, 1.99 mmol) was also added. The solution was stirred at room temperature for 15 min. Ice (1 g) was added. The solution was cooled in an ice-water bath. The solution of diethyl 2-[[2-(benzyloxycarbonylamino)acetyl]amino] propanedioate (730.81 mg, 1.99 mmol) in acetone (20 mL) was added dropwise quickly. Potassium carbonate (saturated solution) (0.6 mL, 3.99 mmol) was added. The pH of the solution was between 5 and 6.5. The solution was stirred at room temperature for 45 min. The solution was extracted with ethyl acetate (2×50 ml). The combined organic solution was washed with water (1 ml) and brine (1 ml), dried over sodium sulfate. The solution was filtered and concentrated. The residue was purified by reverse phase chromatography (C18 column, linerar gradient 5% AcN to 95% AcN in 0.5% aqueous TFA) to give the title compound (383 mg) as colorless oil. MS (ES+) m/z 628.1 [M+H]⁺. 1H NMR (Chloroform-d) δ: 8.37 (d, J=4.5 Hz, 1H), 7.71 (d, J=8.6 Hz, 1H), 7.51-7.65 (m, 2H), 7.46 (d, J=3.5 Hz, 1H), 7.31-7.41 (m, 4H), 5.52 (br. s., 1H), 5.17 (s, 2H), 4.18-4.36 (m, 4H), 3.90 (d, J=5.6 Hz, 1H), 1.20-1.34 (m, 6H).

Step 4: 5-(Benzyloxycarbonylaminomethyl)-1-[4-chloro-2-(3-fluoropyridine-2-carbonyl)phenyl]-1,2,4-triazole-3-carboxylic acid To a solution of diethyl 2-[[2-(benzyloxycarbonylamino)acetyl]amino]-2-[(E)-[4-chloro-2-(3-fluoropyridine-2-carbonyl)phenyl]azo]propanedioate (203 mg, 0.3200 mmol) in THF (10 mL) and methanol (5 mL), potassium carbonate (0.2 mL, 1.29 mmol) was added. Water (2 mL) was added afterwards. After one hour, ethyl acetate (50 ml) was added. The solution was washed with water (2×20 ml), brine (20 ml) and dried over sodium sulfate. The solution was filtered and concentrated to give the title compound (160 mg, 0.3138 mmol, 97.079% yield) as slightly colored oil which was used directly in the next step without further purification. MS (ES+) m/z 510.1 [M+H]⁺.

Step 5: 8-Chloro-6-(3-fluoro-2-pyridyl)-4H-[1,2,4]triazolo[1,5-a][1,4]benzodiazepine-2-carboxylic acid To a stirring solution of 5-(benzyloxycarbonylaminomethyl)-1-[4-chloro-2-(3-fluoropyridine-2-carbonyl)phenyl]-1,2,4-triazole-3-carboxylic acid (170. mg, 0.3300 mmol) in acetic acid (3 mL), hydro bromic acid (1.5 mL, 48% 0.3300 mmol) was added. The solution was heated at 50° C. overnight. The solution was cooled to room temperature and directly purified by reverse phase chromatography (C18 column, linerar gradient 5% AcN to 95% AcN in 0.5% aqueous TFA) to give the title compound (106 mg) as a solid. MS (ES+) m/z 358.0 [M+H]⁺. 1H NMR (DMSO-d6) δ: 8.39 (dt, J=4.5, 1.4 Hz, 1H), 8.32 (s, 1H), 8.00 (d, J=8.8 Hz, 1H), 7.85-7.94 (m, 2H), 7.61 (dt, J=8.7, 4.1 Hz, 1H), 7.50 (d, J=2.3 Hz, 1H), 5.00 (s, 2H).

Example 12: 8-chloro-6-(2-fluorophenyl)-4H-imidazo[1,2-a][1,4]benzodiazepine-2-carboxylic acid

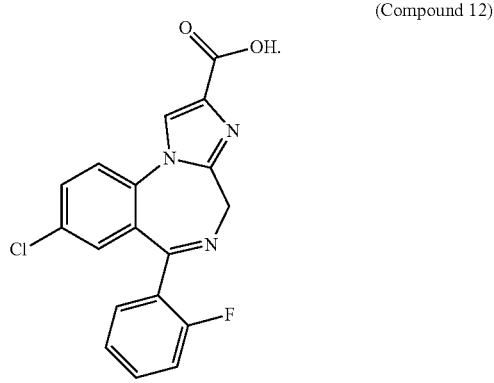 [SMILES: O=C(O)c1cn2c(n1)CN=C(c1ccccc1F)c1cc(Cl)ccc1-2]

(Compound 12)

Step 1: 7-Chloro-5-(2-fluorophenyl)-1,3-dihydro-1,4-benzodiazepine-2-thione

7-Chloro-5-(2-fluorophenyl)-1,3-dihydro-1,4-benzodiazepin-2-one (10 g, 34.64 mmol) and Lawesson's reagent (8.41 g, 20.78 mmol) in toluene (200 ml) were stirred under reflux for 24 hours. The solution was concentrated. Dichloromethane (200 ml) was added. The solution was extracted with water (2×100 ml), brine (100 ml), and dried over sodium sulfate. The solution was filtered and concentrated. The residue was purified by silica gel chromatography eluted with ethyl acetate/hexane (0-30%) to give the title compound (12.17 g) as a slightly colored solid. MS (ES+) m/z 305.0 [M+H]⁺. 1H NMR (CHLOROFORM-d) δ: 8.05-8.16 (m, 1H), 7.58-7.67 (m, 1H), 7.45-7.54 (m, 2H), 7.21-7.31 (m, 2H), 7.16 (d, J=8.6 Hz, 1H), 6.99-7.12 (m, 2H), 4.81 (br. s., 6H), 3.87-3.93 (m, 2H).

Step 2: 7-Chloro-5-(2-fluorophenyl)-2-methylsulfanyl-3H-1,4-benzodiazepine

7-Chloro-5-(2-fluorophenyl)-1,3-dihydro-1,4-benzodiazepine-2-thione (12 g, 35.44 mmol) was dissolved in ethanol (100 mL). The solution was cooled to 0° C., then sodium methoxide (1.43 g, 46.07 mmol) was added. The solution was stirred for 30 min., iodomethane (2.65 mL, 42.52 mmol) was added. The solution was stirred at room temperature overnight then concentrated. The residue was dissolved in ethyl acetate (200 ml) and extracted with water (2×50 ml) and brine (50 ml), then dried over sodium sulfate. The solution was filtered and concentrated. The residue was purified by silica gel chromatography eluted with ethyl acetate/hexane (0-30%) to give the title compound (7.62 g) as colorless oil. MS (ES+) m/z 319.0 [M+H]⁺. 1H NMR (CHLOROFORM-d) δ: 7.51-7.58 (m, 1H), 7.41-7.49 (m, 2H), 7.30-7.35 (m, 1H), 7.18-7.27 (m, 2H), 7.05-7.13 (m, 1H), 2.52 (s, 2H), 1.60 (s, 3H).

Step 3: Methyl 2-[[7-chloro-5-(2-fluorophenyl)-3H-1,4-benzodiazepin-2-yl]amino]-3-hydroxy-propanoate To a stirring solution of 7-chloro-5-(2-fluorophenyl)-2-methylsulfanyl-3H-1,4-benzodiazepine (1.47 g, 4.61 mmol) in toluene (50 mL), L-serine methyl ester hydrochloride (2.15 g, 13.83 mmol), sodium acetate (1.51 g, 18.44 mmol) and acetic acid (0.05 mL, 4.61 mmol) were added. The solution was heated at 90° C. for two hours. The solution was concentrated. The residue was dissolved in ethyl acetate (200 ml). The solution was extracted with water (100 ml), brine (100 ml), dried over sodium sulfate. The solution was filtered and concentrated. The residue was purified by silica gel chromatography eluted with methanol/dichloromethane (0-15%) to give the title compound (330 mg) as slightly colored solid. MS (ES+) m/z 390.0 [M+H]$^+$. 1H NMR (DMSO-d6) δ: 8.11 (d, J=7.6 Hz, 1H), 7.46-7.64 (m, 2H), 7.40 (dd, J=8.6, 2.5 Hz, 1H), 7.31 (td, J=7.6, 1.0 Hz, 1H), 7.24 (dd, J=10.6, 8.3 Hz, 1H), 7.03 (d, J=8.8 Hz, 1H), 6.95 (d, J=2.5 Hz, 1H), 5.12 (t, J=5.6 Hz, 1H), 4.52 (br. s., 1H), 3.59-3.80 (m, 6H), 1.91 (s, 2H).

Step 4: Methyl 2-[[7-chloro-5-(2-fluorophenyl)-3H-1,4-benzodiazepin-2-yl]amino]-3-oxo-propanoate To a stirring solution of oxalyl chloride (0.26 mL, 2.98 mmol) in dichloromethane (20 mL) at −78° C., dimethylsulfoxide (0.32 mL, 4.46 mmol) was added. The solution was stirred at −78° C. for 40 min. Methyl 2-[[7-chloro-5-(2-fluorophenyl)-3H-1,4-benzodiazepin-2-yl]amino]-3-hydroxy-propanoate (580. mg, 1.49 mmol) in dichloromethane (20 mL) was added slowly into the solution. The solution was stirred for another one hour at −78° C. Triethylamine (1.24 mL, 8.93 mmol) was added slowly into the solution with continued stirring at −78° C. for 30 min. and room temperature for 30 min. Dichloromethane (20 ml) was added. The solution was washed with hydrochloric acid (1 N HCl, 2×20 ml), brine (1×30 ml), dried over sodium sulfate. The solution was filtered and concentrated. The residue was used directly in next step.

Step 5: Methyl 8-chloro-6-(2-fluorophenyl)-4H-imidazo[1,2-a][1,4]benzodiazepine-2-carboxylate To a stirring solution of methyl 2-[[7-chloro-5-(2-fluorophenyl)-3H-1,4-benzodiazepin-2-yl]amino]-3-oxo-propanoate (576.99 mg, 1.49 mmol) in toluene (20 mL), acetic anhydride (0.3 mL, 5.95 mmol) was added. The solution was stirred at 110° C. for three hours. The solution was concentrated. The residue was purified by silica gel chromatography eluted with methanol/dichloromethane (0-10%) to give the title compound (220 mg) as dark solid. MS (ES+) m/z 370.0 [M+H]$^+$. 1H NMR (Chloroform-d) δ: 8.10 (s, 1H), 7.61-7.70 (m, 1H), 7.44-7.56 (m, 2H), 7.33-7.38 (m, 1H), 7.20-7.26 (m, 1H), 7.01-7.09 (m, 1H), 5.32 (s, 1H), 4.39 (s, 1H), 3.95 (s, 3H).

Step 6: 8-chloro-6-(2-fluorophenyl)-4H-imidazo[1,2-a][1,4]benzodiazepine-2-carboxylic acid To a stirring solution of methyl 8-chloro-6-(2-fluorophenyl)-4H-imidazo[1,2-a][1,4]benzodiazepine-2-carboxylate (210 mg, 0.5700 mmol) in THF (5 mL) and methanol (5 mL), sodium hydroxide (1.0 M, 1.42 mL, 1.42 mmol) was added. The solution was stirred at room temperature for two hours. The solution was turned to acidic by adding hydrochloric acid (1.0 M). The solution was concentrated. The residue was dissolved in DMF (0.5 ml) and methanol (1.0 ml) and purified by reverse phase chromatography (C18 column, linear gradient 5% AcN to 95% AcN in 0.5% aqueous TFA) to give the title compound (52 mg) as slightly colored solid. MS (ES+) m/z 356.0 [M+H]$^+$. 1H NMR (DMSO-d6) δ: 8.55 (s, 1H), 8.32 (s, 1H), 7.91-7.96 (m, 1H), 7.84 (dd, J=8.8, 2.5 Hz, 1H), 7.53-7.66 (m, 3H), 7.30-7.37 (m, 3H), 7.20-7.28 (m, 1H).

The following exemplary compounds can be prepared by one skilled in the art using methods well-described in the literature. See also CH 574426A5, CH 573931A5, DE2304307A1, DE2234620A1, DE2215943, DE2215943A1, DE2234620A1, DE2304307A1, DE2237592A1, U.S. Pat. Nos. 5,302,715, 3,941,803, incorporated by reference herein in their entireties.

TABLE 1

Exemplary compounds of the present invention

| Number | Name | Structure |
|---|---|---|
| Compound 13 | 8-chloro-6-(2-fluorophenyl)-4-hydroxy-4H-[1,2,4]triazolo[1,5-a][1,4]benzodiazepine-2-carboxylic acid | 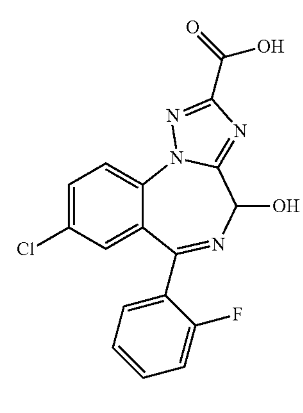 [SMILES: O=C(O)c1nc2n(n1)-c1ccc(Cl)cc1C(c1ccccc1F)=NC2O] |

TABLE 1-continued

Exemplary compounds of the present invention

| Number | Name | Structure |
| --- | --- | --- |
| Compound 14 | 8-chloro-6-(2-fluorophenyl)-4H-imidazo[1,2-a][1,4]benzodiazepine-1-carboxylic acid | 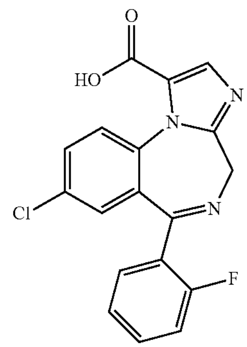 [SMILES: O=C(O)c1cnc2n1-c1ccc(Cl)cc1C(c1ccccc1F)=NC2] |
| Compound 15 | 8-chloro-6-(2-fluorophenyl)-4H-[1,2,4]-triazolo[4,3-a][1,4]benzodiazepine-1-carboxylic acid | 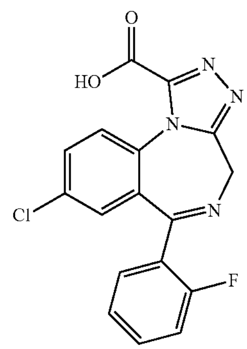 [SMILES: O=C(O)c1nnc2n1-c1ccc(Cl)cc1C(c1ccccc1F)=NC2] |
| Compound 16 | 2-[5-(2-fluorophenyl)-2-oxo-7-(trifluoromethyl)-3H-1,4-benzodiazepin-1-yl]acetic acid | 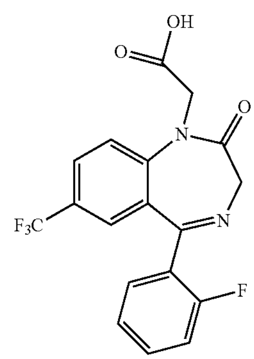 [SMILES: O=C(O)CN1C(=O)CN=C(c2ccccc2F)c2cc(C(F)(F)F)ccc21] |
| Compound 17 | 3-[7-chloro-5-(2-fluorophenyl)-2-oxo-3H-1,4-benzodiazepin-1-yl]propanoic acid | 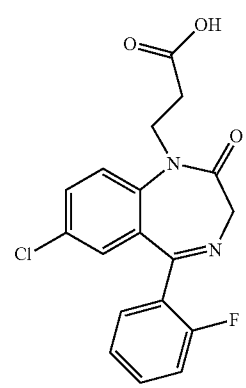 [SMILES: O=C(O)CCN1C(=O)CN=C(c2ccccc2F)c2cc(Cl)ccc21] |

Example 13. Effects of the Compounds and Methods of the Present Invention on Whole Gut Transit Time Dose responses of the effect of Compound 1 on the whole gut transit time (WGTT) were examined. Compound 1 (0, 1, 3 and 10 mg/kg) in 50% propylene glycol was administrated by gavage (5 ml/kg), followed by gavage of 0.2 ml carmine red solution (6% carmine red in 0.5% methylcellulose) into C57B/6 mice. Mice were then placed in a white cardboard box and the time was recorded as time 0. The color of stool was observed every 10 min until the red dye appeared in stool. The time that first red stool appears was recorded as the ending time. The difference between the ending time and time 0 is used to present WGTT (min). As shown in FIG. 1, Compound 1 dose-dependently increased WGTT with a statistical significance at all 1, 3 and 10 mg/kg of Compound 1. These data suggest oral administration of Compound 1 slows the transition in the gastrointestinal system.

Example 14. Effects on Distal Colon Transit Time

Figure 2:
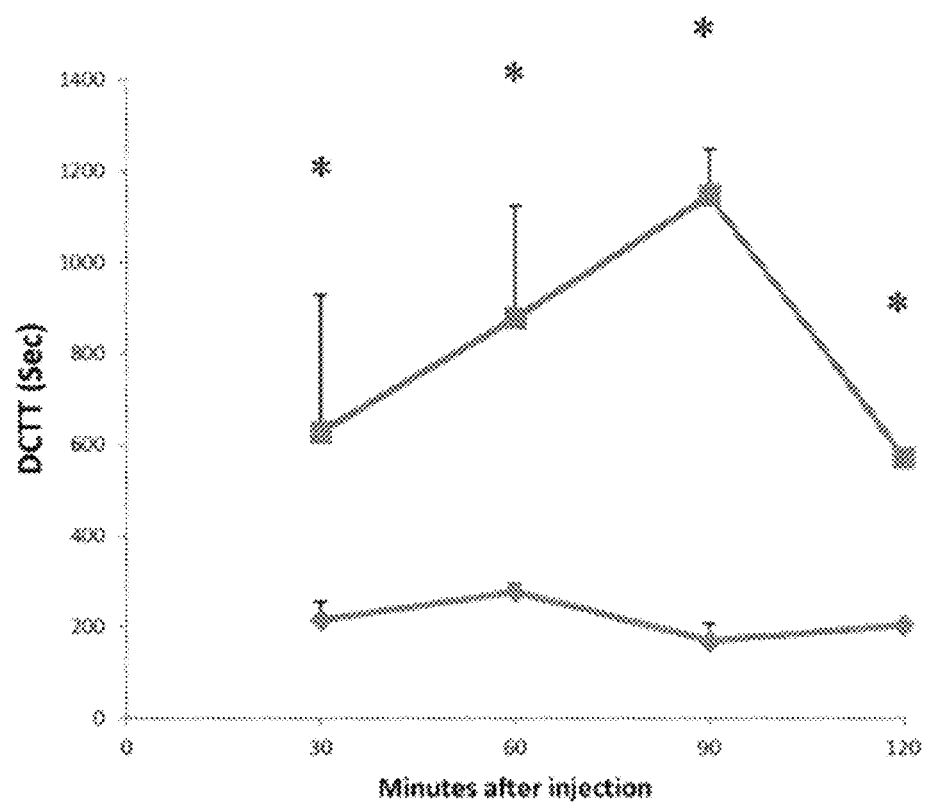
FIG. 2 is a graph showing time course of effect of Compound 1 (squares, 3 mg/kg) on distal colon transit time (DCTT) compared to vehicle (diamonds). Data are presented as mean±SEM (n=7-8). * Significant difference from vehicle group at same time point.

We examined the time course of Compound 1 on distal colon transit time (DCTT) in C57B/6 mice to assess the colon motility. DCTT was performed by gently pushing a 2 mm glass bead into rectal 2 cm and then placing the mouse into a white box (time 0). The time that the glass bead was released from rectal is presented as DCTT (min). Mice were gavaged with 0 or 3 mg/kg of Compound 1 and DTCC was conducted at 30, 60, 90 and 120 min after the administration of Compound 1. Compound 1 (3 mg/kg) significantly increased the DCTT as early as 30 min after the gavage (FIG. 2). The increase in the DCTT reached a peak at 90 mm and returned at 2 hours after the administration of Compound 1 (FIG. 2). The results suggest that oral administration of Compound 1 reduces colon transition, which could be due to reduction of colon motility.

Example 15. Effects on Stool Composition

Figure 3:
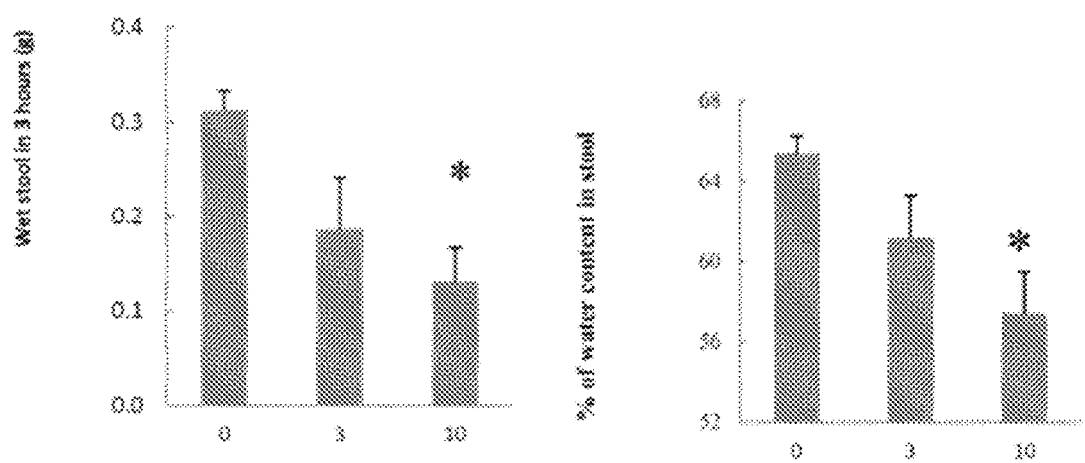
FIG. 3 is a graph that shows the effect of Compound 1 (mg/kg) on stool weight (left) and water content (right). Data are presented as mean±SEM (n=7-8). * Significant difference from vehicle group (0 dose).

After gavage of Compound 1 (3 and 10 mg/kg), stools were collected immediately after expulsion for 3 hours. The wet stools were weighted as total stool weight followed by dry at 65° C. for 24 hours and weight as dry stool weight. The percent of water content in the stool was calculated by (total stool weight−dry stool weight)/total stool weight×100. Treatment with 10 mg/kg, but not 3 mg/kg, of Compound 1 significantly reduced the total stool weight and the percent of water content in the stool (FIG. 3). These data further suggest the reduction of transit, which is consistent with the results of WGTT and DCTT (FIGS. 1 & 2).

Example 16. Pain Sensitivity in IBS Mouse Model

Figure 4:
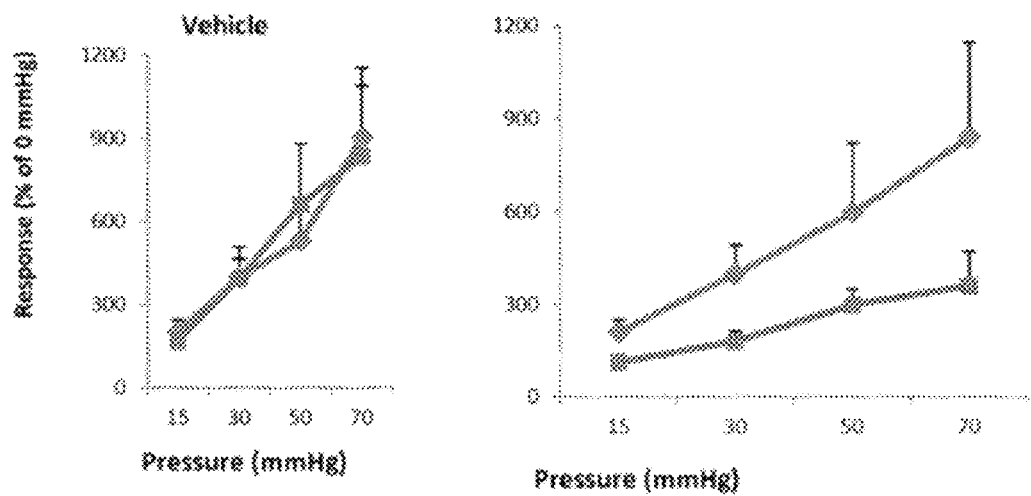
FIG. 4 shows various graphs of treatment with Compound 1 (10 mg/kg) attenuated pain sensitivity in IBS mice. The VMR to CRD was compared between before (left) and after treatment (right) with vehicle (diamonds) or Compound 1 (squares). Data are presented as mean±SEM (n=3-4). The VMR to CRD in IBS mice treated with 10 mg/kg of Compound 1 was significantly reduced when analyzed by Two-Way ANOVA.

IBS visceral pain model, induced by neonatal rectal irritation. Colonic pain sensitivity to graded colorectal balloon distension (CRD, 15, 30, 50 and 70 mmHg) was determined by visceromotor response (VMR) measured by electromyography of external oblique muscle. IBS mice showed a significant increase in pain sensitivity relative to control mice. Treatment with Compound 1 (10 mg/kg) significantly attenuated the hyperalgesia in IBS mice (Two-Way ANOVA, FIG. 4), whereas no effect was observed in control mice (data not shown). These data suggest Compound 1 may be used to treat visceral pain.

Example 17. Measurement of Brain and Plasma Levels

Compound 1 was administered to 5 mice at a dose of 10 mg/kg as a solution in 50% propylene glycol by oral gavage (5 ml/kg), After 30 minutes, mice were sacrificed and plasma and brain were harvested. The concentration of Compound 1 in plasma and brain were measured by LC/MS. Average plasma concentrations were 1061±189 nM, and brain concentration was lower than the limit of quantitation (62.5 nM).

Example 18. Measurement of GABA-A Binding

Potency at the GABA-A receptor can be measured by [$^3$H]flunitrazepam binding to rat cerebral cortex tissue homogenate as described in Speth, R. C, Wastek, G. J., Johnson, P. C., Yamamura, H. I. "Benzodiazepine binding in human brain: Characterization using [$^3$H] flunitrazepam" *Life Sciences* 1978, 22, 859-866, and performed at CEREP (catalog number 0028). Examples 1-12 have a Ki less than 500 nM.

The following references cited above are incorporate herein by reference in their entirety:

1. Everhart J E. The burden of digestive diseases in the United States. US Government Printing Office (NIH Publication No. 09-6443), 2008.
2. Sullivan M A, Cohen S, Snape W J, Jr. Colonic myoelectrical activity in irritable-bowel syndrome. Effect of eating and anticholinergics. N Engl J Med 1978; 298:878-83.
3. Gershon M D. Serotonin and its implication for the management of irritable bowel syndrome. Rev Gastroenterol Disord 2003; 3 Suppl 2:S25-34.
4. Pasricha P J. Desperately seeking serotonin. A commentary on the withdrawal of tegaserod and the state of drug development for functional and motility disorders. Gastroenterology 2007; 132:2287-90.
5. Fargeas M J, Fioramonti J, Bueno L. Central and peripheral action of GABAA and GABAB agonists on small intestine motility in rats. European Journal of Pharmacology 1988; 150:163-169.
6. Grider J R. Interplay of somatostatin, opioid, and GABA neurons in the regulation of the peristaltic reflex. American Journal of Physiology—Gastrointestinal and Liver Physiology 1994; 267:G696-G701.
7. Kerr D I B, Ong J. GABA and GABA-receptors in the enteric nervous system. Neuropharmacology 1984; 23:835-836.
8. Krantis A. GABA in the mammalian enteric nervous system. News in Physiological Sciences 2000; 15:284-290.
9. Krantis A, Costa M, Furness J B, Orbach J. γ-Aminobutyric acid stimulates intrinsic inhibitory and excitatory nerves in the guinea-pig intestine. European Journal of Pharmacology 1980; 67:461-466.
10. Ong J, Kerr D I B. Evidence for a physiological role of GABA in the control of guinea-pig intestinal motility. Neuroscience Letters 1984; 50:339-343.
11. Reis H J, Berghe P V, Romano-Silva M A, Smith T K. GABA-induced calcium signaling in cultured enteric neurons is reinforced by activation of cholinergic pathways. Neuroscience 2006; 139:485-494.
12. Williamson S, Faulkner-Jones B E, Cram D S, Furness J B, Harrison L C. Transcription and translation of two glutamate decarboxylase genes in the ileum of rat, mouse and guinea pig. Journal of the Autonomic Nervous System 1995; 55:18-28.

13. Williamson S, Pompolo S, Furness J B. GABA and nitric oxide synthase immunoreactivities are colocalized in a subset of inhibitory motor neurons of the guinea-pig small intestine. Cell and Tissue Research 1996; 284:29-37.
14. Salari P, Abdollahi M. Systematic review of modulators of benzodiazepine receptors in irritable bowel syndrome: is there hope? World J Gastroenterol 2011; 17:4251-7.
15. Ritchie J A, Truelove S C. Treatment of irritable bowel syndrome with lorazepam, hyoscine butylbromide, and ispaghula husk. Br Med J 1979; 1:376-8.
16. Pace F, Maurano A, Ciacci C, Savarino V, Attili A, Iaquinto G, Magni E, Porro G B. Octatropine methyl bromide and diazepam combination (Valpinax) in patients with irritable bowel syndrome: a multicentre, randomized, placebo-controlled trial. Eur Rev Med Pharmacol Sci 2010; 14:155-62.
17. Talley N J. Evaluation of drug treatment in irritable bowel syndrome. British Journal of Clinical Pharmacology 2003; 56:362-369.
18. Horvath K, Andrasi F, Berzsenyi P, Patfalusi M, Patthy M, Szabo G, Sebestyen L, Bagdy E, Korosi J, Botka P, Hamori T, Lang T. A New Psychoactive 5h-2,3-Benzodiazepine with a Unique Spectrum of Activity. Arzneimittel-Forschung/Drug Research 1989; 39-2:894-899.
19. Mennini T, Abbiati A, Caccia S, Cotecchia S, Gomez A, Garattini S. Brain Levels of Tofizopam in the Rat and Relationship with Benzodiazepine Receptors. Naunyn-Schmiedebergs Archives of Pharmacology 1982; 321: 112-115.
20. Bagal S K, Bungay P J. Minimizing Drug Exposure in the CNS while Maintaining Good Oral Absorption. Acs Medicinal Chemistry Letters 2012; 3:948-950.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula 1, or a pharmaceutically acceptable salt thereof:

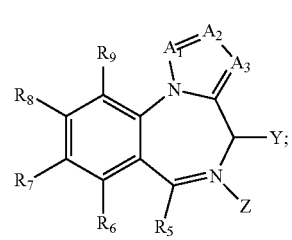

wherein: $A_1$, $A_2$, and $A_3$ are independently selected from C or N,
where $A_3$ is N;
each of $A_1$ and $A_2$ is a C unsubstituted or substituted with a group consisting of alkyl, alkenyl, alkynyl, cycloalkyl, heterocycloalkyl, aryl, heteroaryl, $-COOR_{10}$, $-COR_{10}$, $-OR_{10}$, $-SR_{10}$, $-NR_{10}R_{11}$, and $-CONR_{10}R_{11}$;
wherein one of $A_1$ and $A_2$ is C substituted with $-COOR_{10}$ or $-CONR_{10}R_{11}$;
each of $R_{10}$ and $R_{11}$ is independently H, alkyl, alkenyl, alkynyl, cycloalkyl, heterocycloalkyl, aryl, or heteroaryl optionally substituted with one or more amidinyl, guanidinyl, phosphate, sulfate, tetrazole, 3-hydroxyisoxazole, urea, primary amides, sulfonamides, sulfonyl ureas, acylamidines, acylguanidines, or $-NR_{12}R_{13}$ groups;
each of $R_{12}$ and $R_{13}$ is independently H, $-CONH_2$, $-SOONH_2$, alkyl, alkenyl, alkynyl, cycloalkyl, heterocycloalkyl, aryl, or heteroaryl;
Y is selected from H and OH;
Z is selected from oxygen and an electron lone pair;
$R_5$ is selected from the group consisting of aryl, heteroaryl, or cycloalkenyl groups substituted with one or more halo, $CF_3$, CN, $NO_2$, $C_{1-4}$ alkyl, $C_{2-4}$ alkenyl, $C_{2-4}$ alkynyl, OH, OR (where R is $C_{1-4}$ alkyl or $C_{1-4}$ fluoroalkyl), and $SO_2R$ (where R is $C_{1-4}$ alkyl or $C_{1-4}$ fluoroalkyl); and
$R_6$, $R_7$, $R_8$, $R_9$ are each independently selected from the group consisting of H, halo, $CF_3$, CN, $NO_2$, $C_{2-4}$ alkenyl, $C_{2-4}$ alkynyl, OH, OR (where R is $C_{1-4}$ alkyl or $C_{1-4}$ fluoroalkyl), and $SO_2R$ (where R is $C_{1-4}$ alkyl or $C_{1-4}$ fluoroalkyl).

2. A pharmaceutical composition comprising a compound of claim 1 or a pharmaceutically acceptable salt thereof, and a pharmaceutically acceptable carrier.

3. A method of treating visceral pain in a subject in need thereof, comprising administering a therapeutically effective amount of the compound as claimed in claim 1, or a pharmaceutically acceptable salt thereof, to the subject.

4. A method of treating irritable bowel syndrome in a subject in need thereof, comprising administering a therapeutically effective amount of the compound as claimed in claim 1, or a pharmaceutically acceptable salt thereof, to the subject.

5. A method of treating functional abdominal pain, functional idiopathic diarrhea, inflammatory bowel diseases, drug induced pain, bile salt malabsorption, or lactase or other carbohydrate intolerance in a subject in need thereof, comprising administering a therapeutically effective amount of the compound as claimed in claim 1, or a pharmaceutically acceptable salt thereof, to the subject.

6. A method of treating visceral pain in a subject in need thereof, comprising administering a therapeutically effective amount of the pharmaceutical composition as claimed in claim 2 to the subject.

7. A method of treating irritable bowel syndrome in a subject in need thereof, comprising administering a therapeutically effective amount of the pharmaceutical composition as claimed in claim 2 to the subject.

8. A method of treating functional abdominal pain, functional idiopathic diarrhea, inflammatory bowel diseases, drug induced pain, bile salt malabsorption, or lactase or other carbohydrate intolerance in a subject in need thereof, comprising administering a therapeutically effective amount of the pharmaceutical composition as claimed in claim 2 to the subject.

9. The compound of claim 1, wherein $A_1$ is C substituted with —COOH.

10. The compound of claim 1, wherein $A_2$ is C substituted with —COOH.

11. A pharmaceutically acceptable salt of a compound of formula 1:

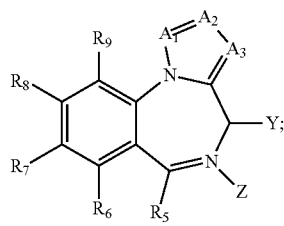

1 wherein:

$A_1$, $A_2$, and $A_3$ are independently selected from C or N, where $A_3$ is N;

each of $A_1$ and $A_2$ is a C unsubstituted or substituted with a group consisting of alkyl, alkenyl, alkynyl, cycloalkyl, heterocycloalkyl, aryl, heteroaryl, —$COOR_{10}$, —$COR_{10}$, —$OR_{10}$, —$SR_{10}$, —$NR_{10}R_{10}$, and —$CONR_{10}R_{11}$;

wherein one of $A_1$ and $A_2$ is C substituted with —$COOR_{10}$ or —$CONR_{10}R_{11}$;

each of $R_{10}$ and $R_{11}$ is independently H, alkyl, alkenyl, alkynyl, cycloalkyl, heterocycloalkyl, aryl, or heteroaryl optionally substituted with one or more amidinyl, guanidinyl, phosphate, sulfate, tetrazole, 3-hydroxyisoxazole, urea, primary amides, sulfonamides, sulfonyl ureas, acylamidines, acylguanidines, or —$NR_{12}R_{13}$ groups;

each of $R_{12}$ and $R_{13}$ is independently H, —$CONH_2$, —$SOONH_2$, alkyl, alkenyl, alkynyl, cycloalkyl, heterocycloalkyl, aryl, or heteroaryl;

Y is selected from H and OH;

Z is selected from oxygen and an electron lone pair;

$R_5$ is selected from the group consisting of aryl, heteroaryl, or cycloalkenyl groups substituted with one or more halo, $CF_3$, CN, $NO_2$, $C_{1-4}$ alkyl, $C_{2-4}$ alkenyl, $C_{2-4}$ alkynyl, OH, OR (where R is $C_{1-4}$ alkyl or $C_{1-4}$ fluoroalkyl), and $SO_2R$ (where R is $C_{1-4}$ alkyl or $C_{1-4}$ fluoroalkyl); and $R_6$, $R_7$, $R_8$, $R_9$ are each independently selected from the group consisting of H, halo, $CF_3$, CN, $NO_2$, $C_{2-4}$ alkenyl, $C_{2-4}$ alkynyl, OH, OR (where R is $C_{1-4}$ alkyl or $C_{1-4}$ fluoroalkyl), and $SO_2R$ (where R is $C_{1-4}$ alkyl or $C_{1-4}$ fluoroalkyl).

12. The salt of claim 11, wherein the salt is a pharmaceutically acceptable salt of an acidic compound of formula 1.

13. The salt of claim 11, wherein the salt is selected from the group consisting of an aluminum salt, an ammonium salt, a calcium salt, a copper salt, a ferric salt, a ferrous salt, a lithium salt, a magnesium salt, a manganic salt, a manganous salt, a potassium salt, a sodium salt, and a zinc salt.

14. The salt of claim 11, wherein $A_1$ is C substituted with an acidic group.

15. The salt of claim 11, wherein $A_2$ is C substituted with an acidic group.

16. A pharmaceutical composition comprising the salt as claimed in claim 11, and a pharmaceutically acceptable carrier.

17. A method of treating visceral pain in a subject in need thereof, comprising administering a therapeutically effective amount of the salt as claimed in claim 11 to the subject.

18. A method of treating irritable bowel syndrome in a subject in need thereof, comprising administering a therapeutically effective amount of the salt as claimed in claim 11 to the subject.

19. A method of treating functional abdominal pain, functional idiopathic diarrhea, inflammatory bowel diseases, drug induced pain, bile salt malabsorption, or lactase or other carbohydrate intolerance in a subject in need thereof, comprising administering a therapeutically effective amount of the salt as claimed in claim 11 to the subject.

20. A method of treating visceral pain in a subject in need thereof, comprising administering a therapeutically effective amount of a pharmaceutical composition as claimed in claim 16 to the subject.

21. A method of treating irritable bowel syndrome in a subject in need thereof, comprising administering a therapeutically effective amount of a pharmaceutical composition as claimed in claim 16 to the subject.

22. A method of treating functional abdominal pain, functional idiopathic diarrhea, inflammatory bowel diseases, drug induced pain, bile salt malabsorption, or lactase or other carbohydrate intolerance in a subject in need thereof, comprising administering a therapeutically effective amount of a pharmaceutical composition as claimed in claim 16 to the subject.

* * * * *